United States Patent

Seitz et al.

Patent Number: 5,244,865
Date of Patent: Sep. 14, 1993

[54] SUBSTITUTED IMIDAZOLINYLPYRIMIDINES

[75] Inventors: Thomas Seitz, Monheim; Klaus Lürssen/, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 891,493

[22] Filed: May 29, 1992

[30] Foreign Application Priority Data

Jun. 7, 1991 [DE] Fed. Rep. of Germany ....... 4118720

[51] Int. Cl.$^5$ ............... C07D 401/14; C07D 403/04; C07D 403/14; A01N 43/54
[52] U.S. Cl. .................................. 504/239; 504/242; 504/243; 544/316; 544/331; 544/333; 544/310; 544/319
[58] Field of Search ............... 544/316, 331, 333, 310, 544/319; 504/239, 242, 243

[56] References Cited

FOREIGN PATENT DOCUMENTS 0202654 5/1986 European Pat. Off. .
0215738 9/1986 European Pat. Off. .

Primary Examiner—John M. Ford
Attorney, Agent, or Firm—Sprung Horn Kramer & Woods

[57] ABSTRACT

Herbicidal new substituted imidazolinylpyrimidines of the general formula (I)

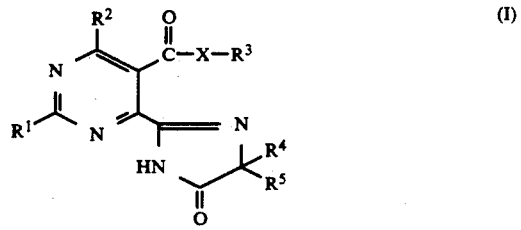

in which
$R^1$ represents hydrogen, halogen, cyano, nitro or thiocyanato, or represents a hydroxyl, mercapto, amino, carbonyl, sulphinyl, sulphonyl, alkyl, alkenyl, alkinyl, cycloalkyl, cycloalkenyl, aryl or heterocyclyl radical, each of which is optionally substituted,
$R^2$ represents hydrogen, hydroxyl, halogen, alkyl or halogenoalkyl,
$R^3$ represents hydrogen, or represents alkyl, alkenyl, alkinyl, cycloalkyl, cycloalkenyl, aryl or heterocyclyl, each of which is optionally substituted, or represents an equivalent of an inorganic or organic cation,
$R^4$ and $R^5$ independently of each other in each case represent hydrogen, alkyl, halogenoalkyl or cycloalkyl and
X represents oxygen or sulphur.

11 Claims, No Drawings

SUBSTITUTED IMIDAZOLINYLPYRIMIDINES

The invention relates to novel substituted imidazolinylpyrimidines, to a plurality of processes for their preparation, and to their use as herbicides.

It has been disclosed that certain imidazolinylpyridines such as, for example, the compound methyl 2-(4,4-dimethylimidazolin-5-on-2-yl)-pyridine-3-carboxylate, have herbicidal properties (compare, for example, EP 41,623).

However, the herbicidal activity of these previously known compounds towards problem weds as well as their compatibility with important crop plants is not entirely satisfactory in all fields of application.

New imidazolinylpyrimidines have been found of the general formula (I)

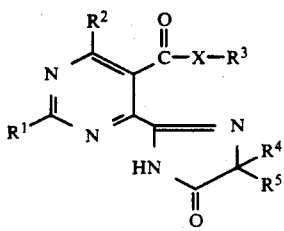
(I)

in which

R$^1$ represents hydrogen, halogen, cyano, nitro or thiocyanato, or represents a hydroxyl, mercapto, amino, carbonyl, sulphinyl, sulphonyl, alkyl, alkenyl, alkinyl, cycloalkyl, cycloalkenyl, aryl or heterocyclyl radical, each of which is optionally substituted, R$^2$ represents hydrogen, hydroxyl, halogen, alkyl or halogenoalkyl, R$^3$ represents hydrogen, or represents alkyl, alkenyl, alkinyl, cycloalkyl, cycloalkenyl, aryl or heterocyclyl, each of which is optionally substituted, or represents an equivalent of an inorganic or organic cation, R$^4$ and R$^5$ independently of each other in each case represent hydrogen, alkyl, halogenoalkyl or cycloalkyl and X represents oxygen or sulphur.

If appropriate, the compounds of the formula (I) can exist as geometric and/or optical isomers or mixtures of isomers of various compositions, depending on the nature of the substituents. The invention claims the pure isomers as well as the mixtures of isomers.

Furthermore, it has been found that the new imidazolinylpyrimidines of the general formula (I)

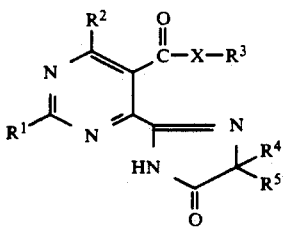
(I)

in which

R$^1$ represents hydrogen, halogen, cyano, nitro or thiocyanato, or represents a hydroxyl, mercapto, amino, carbonyl, sulphinyl, sulphonyl, alkyl, alkenyl, alkinyl, cycloalkyl, cycloalkenyl, aryl or heterocyclyl radical, each of which is optionally substituted, R$^2$ represents hydrogen, hydroxyl, halogen, alkyl or halogenoalkyl, R$^3$ represents hydrogen, or represents alkyl, alkenyl, alkinyl, cycloalkyl, cycloalkenyl, aryl or heterocyclyl, each of which is optionally substituted, or represents an equivalent of an inorganic or organic cation, R$^4$ and R$^5$ independently of each other in each case represent hydrogen, alkyl, halogenoalkyl or cycloalkyl and X represents oxygen or sulphur, are obtained when (a) pyrimidine-4,5-dicarboxylates of the formula (II)

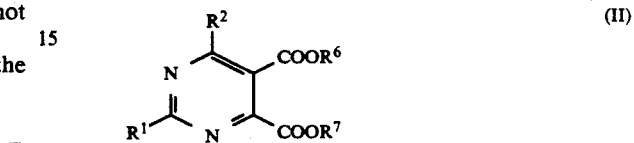
(II)

in which

R$^1$ and R$^2$ have the abovementioned meaning and

R$^6$ and R$^7$ independently of each other in each case represent alkyl, are reacted with α-amino acid amides of the formula (III)

(III)

in which

R$^4$ and R$^5$ have the abovementioned meaning, if appropriate in the presence of a diluent and if appropriate in the presence of a reaction auxiliary and, if appropriate, (b) the imidazolinylpyrimidinecarboxylic acids which can thus be obtained, of the formula (Ia)

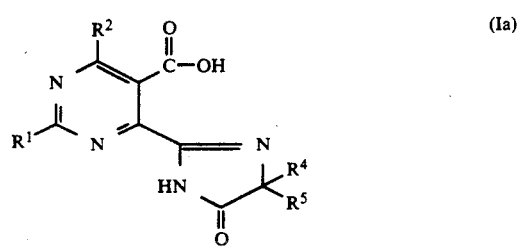
(Ia)

in which

R$^1$, R$^2$, R$^4$ and R$^5$ have the abovementioned meaning, are subjected to a subsequent reaction and first reacted, in a 1st step, with a condensing agent, if appropriate in the presence of a diluent and if appropriate in the presence of a reaction auxiliary, and the imidazo-pyrrolo-pyrimidines which can thus be obtained, of the formulae (IVa) and (IVb)

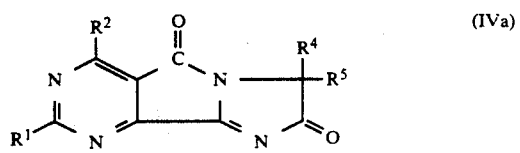
(IVa)

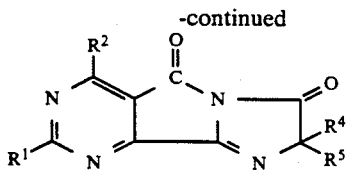

in which

R¹, R², R⁴ and R⁵ have the abovementioned meaning, are reacted, in a subsequent 2nd step, with alcohols or thiols of the formula (V)

in which

R³ and X have the abovementioned meaning,
if appropriate in the presence of a diluent and if appropriate in the presence of a reaction auxiliary.

Finally, it has been found that the new imidazolinylpyrimidines of the general formula (I) as well as the imidazo-pyrrolo-pyrimidines of the general formulae (IVa) and (IVb), which are termed intermediates, have herbicidal properties.

Surprisingly, the imidazolinylpyrimidines of the general formula (I) according to the invention show a considerably better herbicidal activity against problem weeds and simultaneously an equally good compatibility with important crop plants when compared with the imidazolinylpyridines known from the prior art such as, for example, the compound methyl 2-(4,4-dimethylimidazolin-5-on-2-yl)-pyridine-3-carboxylate, which are similar compounds chemically and from the point of view of their action. Formula (I) provides a general definition of the imidazolinylpyrimidines according to the invention. Preferred compounds of the formula (I) are those in which R¹ represents hydrogen, fluorine, chlorine, bromine, iodine, cyano, nitro or thiocyanato;
and furthermore represents in each case optionally substituted hydroxyl or mercapto, suitable substituents in each case being: straight-chain or branched alkyl having 1 to 8 carbon atoms, straight-chain or branched halogenoalkyl having 1 to 8 carbon atoms and 1 to 17 identical or different halogen atoms, straight-chain or branched alkoxyalkyl having in each case 1 to 8 carbon atoms in the individual alkyl moieties, straight-chain or branched dialkylaminoalkyl having in each case 1 to 8 carbon atoms in the individual alkyl moieties, straight-chain or branched alkanoyl having 1 to 9 carbon atoms, straight-chain or branched alkoxycarbonyl having 2 to 9 carbon atoms, straight-chain or branched alkylsulphonyl having 1 to 8 carbon atoms, straight-chain or branched alkoxysulphonyl having 1 to 8 carbon atoms, or arylalkyl which has 1 to 8 carbon atoms in the straight-chain or branched alkyl moiety and 6 to 10 carbon atoms in the aryl moiety, aryl having 6 to 10 carbon atoms, arylcarbonyl, arylsulphonyl or aryloxysulphonyl having in each case 6 to 10 carbon atoms in the aryl moiety, heterocyclyl or heterocyclylalkyl having in each case 2 to 9 carbon atoms and 1 to 5 identical or different hetero atoms, in particular nitrogen, oxygen and/or sulphur in the heterocyclyl moiety and, if appropriate, 1 to 4 carbon atoms in the straight-chain or branched alkyl moiety and each of these arylalkyl, aryl, arylcarbonyl, arylsulphonyl, aryloxysulphonyl, heterocyclyl or heterocyclylalkyl is optionally monosubstituted or polysubstituted in the aryl or heterocyclyl moiety, by identical or different substituents, suitable aryl or heterocyclyl substituents in each case being: halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and also phenyl which is optionally monosubstituted or polysubstituted by identical or different substituents from the series comprising halogen and/or straight-chain or branched alkyl having 1 to 4 carbon atoms;
and furthermore represents amino which is optionally monosubstituted or disubstituted by identical or different substituents, suitable substituents being: straight-chain or branched alkyl having 1 to 8 carbon atoms, straight-chain or branched alkenyl having 2 to 8 carbon atoms, straight-chain or branched alkinyl having 2 to 8 carbon atoms, straight-chain or branched halogenoalkyl having 1 to 8 carbon atoms and 1 to 17 identical or different halogen atoms, straight-chain or branched alkoxyalkyl having in each case 1 to 8 carbon atoms in the individual alkyl moieties, straight-chain or branched dialkylaminoalkyl, having in each case 1 to 8 carbon atoms in the individual alkyl moieties, straight-chain or branched alkanoyl having 1 to 9 carbon atoms, straight-chain or branched alkoxycarbonyl having 2 to 9 carbon atoms, straight-chain or branched alkylsulphonyl having 1 to 8 carbon atoms, straight-chain or branched alkoxysulphonyl having 1 to 8 carbon atoms, straight-chain or branched dialkylaminosulphonyl having in each case 1 to 8 carbon atoms in the individual alkyl moieties, or arylalkyl which has 1 to 8 carbon atoms in the straight-chain or branched alkyl moiety and 6 to 10 carbon atoms in the aryl moiety, aryl having 6 to 10 carbon atoms, arylcarbonyl, arylsulphonyl or aryloxysulphonyl, each of which has 6 to 10 carbon atoms in the aryl moiety, heterocyclyl or heterocyclylalkyl, each of which has 2 to 9 carbon atoms and 1 to 5 identical or different hetero atoms, in particular nitrogen, oxygen and/or sulphur in the heterocyclyl moiety and, if appropriate, 1 to 4 carbon atoms in the straight-chain or branched alkyl moiety and each of these arylalkyl, aryl, arylcarbonyl, arysulphonyl, aryoxysulphonyl, heterocyclyl or heterocyclylalkyl is optionally monosubstituted or polysubstituted in the aryl or heterocyclyl moiety by identical or different substituents, suitable aryl or heterocyclyl substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and, if appropriate, phenyl which is optionally monosubstituted or polysubstituted by identical or different substituents from the series comprising halogen and/or straight-chain or branched alkyl having 1 to 4 carbon atoms;

and furthermore represents a carbonyl, sulphinyl or sulphonyl group, each of which is substituted, suitable substituents in each case being:

hydrogen, hydroxyl, amino, in each case straight-chain or branched alkyl, alkoxy, alkylamino or dialkylamino, each of which has 1 to 8 carbon atoms in the individual alkyl moieties, in each case straight-chain or branched halogenoalkyl or halogenoalkoxy, each of which has 1 to 8 carbon atoms and 1 to 17 identical or different halogen atoms, or aryl, aryloxy, arylamino or diarylamino, each of which has 6 to 10 carbon atoms in the individual aryl moieties and each of which is optionally monosubstituted or polysubstituted in the aryl moiety by identical or different substituents, suitable substituents in the individual aryl moieties in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents from the series comprising halogen and/or straight-chain or branched alkyl having 1 to 4 carbon atoms;

and furthermore represents straight-chain or branched alkyl which has 1 to 8 carbon atoms and which is optionally monosubstituted or polysubstituted by identical or different substituents, suitable substituents being:

fluorine, chlorine, bromine, iodine, hydroxyl, cyano, nitro, aminocarbonyl, formamido, in each case straight-chain or branched alkoxy, halogenoalkoxy, alkylthio, halogenoalkylthio, alkylamino, dialkylamino, alkanoyl, N-alkylaminocarbonyl, N,N-dialkylaminocarbonyl, alkanoylamido or alkylsulphonyl, each of which has 1 to 8 carbon atoms in the individual alkyl moieties and, if appropriate, 1 to 17 identical or different halogen atoms, or aryl, aryloxy, arylthio, arylamino, diarylamino, arylcarbonyl or arylsulphonyl, each of which has 6 to 10 carbon atoms in the individual aryl moieties and each of which is optionally monosubstituted or polysubstituted in the aryl moiety by identical or different substituents, or heterocyclyl having 2 to 9 carbon atoms and 1 to 5 identical or different hetero atoms, in particular nitrogen, oxygen and/or sulphur, which is optionally monosubstituted or polysubstituted by identical or different substituents, suitable aryl or heterocyclyl substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents from the series comprising halogen and/or straight-chain or branched alkyl having 1 to 4 carbon atoms;

and furthermore represents straight-chain or branched alkenyl which has 2 to 8 carbon atoms and which is optionally monosubstituted or polysubstituted by identical or different substituents, suitable substituents being: fluorine, chlorine, bromine, iodine or cyano;

and furthermore represents straight-chain or branched alkinyl which has 2 to 8 carbon atoms and which is optionally monosubstituted or polysubstituted by identical or different substituents, suitable substituents being: fluorine, chlorine, bromine or iodine;

and furthermore represents cycloalkyl or cycloalkenyl, each of which has 3 to 8 carbon atoms and each of which is optionally monosubstituted or polysubstituted by identical or different substituents, suitable substituents in each case being:

fluorine, chlorine, bromine, iodine, and in each case straight-chain or branched alkyl or halogenoalkyl, each of which has 1 to 8 carbon atoms and, if appropriate, 1 to 17 identical or different halogen atoms;

and furthermore represents aryl which has 6 to 10 carbon atoms or heterocyclyl having 2 to 9 carbon atoms and 1 to 5 identical or different hetero atoms, in particular nitrogen, oxygen and/or sulphur, and each aryl or heterocyclyl is optionally monosubstituted or polysubstituted by identical or different substituents, suitable aryl or heterocyclyl substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents from the series comprising halogen and/or straight-chain or branched alkyl having 1 to 4 carbon atoms;

$R^2$ represents hydrogen, hydroxyl, fluorine, chlorine, bromine, iodine, straight-chain or branched alkyl having 1 to 8 carbon atoms or straight-chain or branched halogenoalkyl having 1 to 8 carbon atoms and 1 to 17 identical or different halogen atoms, $R^3$ represents hydrogen or an equivalent of an alkali metal cation, alkaline earth metal cation or an ammonium cation which is optionally monosubstituted or polysubstituted by identical or different substituents from the series comprising straight-chain or branched alkyl having 1 to 18 carbon atoms and/or benzyl, and furthermore represents straight-chain or branched alkyl which has 1 to 18 carbon atoms and which is optionally monosubstituted or polysubstituted by identical or different substituents, suitable substituents being: fluorine, chlorine, bromine, iodine, hydroxyl, cyano, nitro, aminocarbonyl, formamido, in each case straight-chain or branched alkoxy, halogenoalkoxy, alkylthio, halogenoalkylthio, alkylamino, dialkylamino, alkanoyl, N-alkylaminocarbonyl, N,N-dialkylaminocarbonyl, alkanoylamido or alkylsulphonyl, each of which has 1 to 8 carbon atoms in the individual alkyl moieties and, if appropriate, 1 to 17 identical or different halogen atoms, or aryl, aryloxy, arylthio, arylamino, diarylamino, arylcarbonyl or arylsulphonyl, each of which has 6 to 10 carbon atoms in the individual aryl moieties and each of which is optionally monosubstituted or polysubstituted in the aryl moiety by identical or different substituents, or heterocyclyl having 2 to 9 carbon atoms and 1 to 5 identical or different hetero atoms, in particular nitrogen, oxygen and/or sulphur, which is optionally monosubstituted or polysubstituted by identical or different substituents, suitable aryl or heterocyclyl substituents in each case being: halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents from the series comprising halogen and/or straight-chain or branched alkyl having 1 to 4 carbon atoms;

and furthermore represents straight-chain or branched alkenyl which has 2 to 8 carbon atoms and which is optionally monosubstituted or polysubstituted by identical or different substituents, suitable substituents being:

fluorine, chlorine, bromine, iodine or cyano, or aryl which has 6 to 10 carbon atoms and which is optionally monosubstituted or polysubstituted by identical or different substituents, suitable substituents being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms;

and furthermore represents straight-chain or branched alkinyl which has 2 to 8 carbon atoms and which is optionally monosubstituted or polysubstituted by identical or different substituents, suitable substituents being: fluorine, chlorine, bromine or iodine;

and furthermore represents cycloalkyl or cycloalkenyl, each of which has 3 to 8 carbon atoms and each of which is optionally monosubstituted or polysubstituted by identical or different substituents, suitable substituents in each case being:

fluorine, chlorine, bromine, iodine, and in each case straight-chain or branched alkyl or halogenoalkyl, each of which has 1 to 8 carbon atoms and, if appropriate, 1 to 17 identical or different halogen atoms;

and furthermore represents aryl which has 6 to 10 carbon atoms or heterocyclyl having 2 to 9 carbon atoms and 1 to 5 identical or different hetero atoms, in particular nitrogen, oxygen and/or sulphur, and each aryl or heterocyclyl is optionally monosubstituted or polysubstituted by identical or different substituents, suitable aryl or heterocyclyl substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents from the series comprising halogen and/or straight-chain or branched alkyl having 1 to 4 carbon atoms;

$R^4$ and $R^5$ independently of each other in each case represent hydrogen, straight-chain or branched alkyl having 1 to 8 carbon atoms, straight-chain or branched halogenoalkyl having 1 to 8 carbon atoms and 1 to 17 identical or different halogen atoms, or cycloalkyl having 3 to 8 carbon atoms and X represents oxygen or sulphur.

Particularly preferred compounds of the formula (I) are those in which $R^1$ represents hydrogen, fluorine, chlorine, bromine, iodine, cyano, nitro or thiocyanato; and furthermore represents in each case optionally substituted hydroxyl or mercaoto, suitable substituents in each case being:

straight-chain or branched alkyl having 1 to 4 carbon atoms, straight-chain or branched halogenoalkyl having 1 to 4 carbon atoms and 1 to 9 identical or different halogen atoms, straight-chain or branched alkoxyalkyl having in each case 1 to 4 carbon atoms in the individual alkyl moieties, straight-chain or branched dialkylaminoalkyl having in each case 1 to 4 carbon atoms in the individual alkyl moieties, straight-chain or branched alkanoyl having 1 to 5 carbon atoms, straight-chain or branched alkoxycarbonyl having 2 to 5 carbon atoms, straight-chain or branched alkylsulphonyl having 1 to 4 carbon atoms, straight-chain or branched alkoxysulphonyl having 1 to 4 carbon atoms, or arylalkyl which has 1 to 4 carbon atoms in the straight-chain or branched alkyl moiety and 6 or 10 carbon atoms in the aryl moiety, aryl which has 6 or 10 carbon atoms, arylcarbonyl, arylsulphonyl or aryloxysulphonyl, each of which has 6 or 10 carbon atoms in the aryl moiety, heterocyclyl or heterocyclylalkyl, each of which has 2 to 9 carbon atoms and 1 to 4 identical or different hetero atoms, in particular nitrogen, oxygen and/or sulphur in the heterocyclyl moiety and, if appropriate, 1 to 4 carbon atoms in the straight-chain or branched alkyl moiety, and each of these arylalkyl, aryl, arylcarbonyl, arylsulphonyl, aryloxysulphonyl, heterocyclyl or heterocyclylalkyl is optionally monosubstituted to pentasubstituted in the aryl or heterocyclyl moiety by identical or different substituents, suitable aryl or heterocyclyl substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted to pentasubstituted by identical or different substituents from the series comprising halogen and/or straight-chain or branched alkyl having 1 to 4 carbon atoms;

and furthermore represents amino which is optionally monosubstituted or disubstituted by identical or different substituents, suitable substituents being: straight-chain or branched alkyl having 1 to 4 carbon atoms, straight-chain or branched alkenyl having 2 to 5 carbon atoms, straight-chain or branched alkinyl having 2 to 5 carbon atoms, straight-chain or branched halogenoalkyl having 1 to 4 carbon atoms and 1 to 9 identical or different halogen atoms, straight-chain or branched alkoxyalkyl having in each case 1 to 4 carbon atoms in the individual alkyl moieties, straight-chain or branched dialkylaminoalkyl, having in each case 1 to 4 carbon atoms in the individual alkyl moieties, straight-chain or branched alkanoyl having 1 to 5 carbon atoms, straight-chain or branched alkoxycarbonyl having 2 to 5 carbon atoms, straight-chain or branched alkylsulphonyl having 1 to 4 carbon atoms, straight-chain or branched alkoxysulphonyl having 1 to 4 carbon atoms, straight-chain or branched dialkylaminosulphonyl having in each case 1 to 4 carbon atoms in the individual alkyl moieties, or arylalkyl which has 1 to 4 carbon atoms in the straight-chain or branched alkyl moiety and 6 or 10 carbon atoms in the aryl moiety, aryl having 6 or 10 carbon atoms, arylcarbonyl, arylsulphonyl or aryloxysulphonyl, each of which has 6 or 10 carbon atoms in the aryl moiety, heterocyclyl or heterocyclylalkyl, each of which has 2 to 9 carbon atoms and 1 to 4 identical or different hetero atoms, in particular nitrogen, oxygen and/or sulphur in the heterocyclyl moiety and, if appropriate, 1 to 4 carbon atoms in the straight-chain or branched alkyl moiety, and each of these arylalkyl, aryl, arylcarbonyl, arylsulphonyl, aryloxysulphonyl, heterocyclyl and heterocyclylalkyl is optionally monosubstituted to pentasubstituted in the aryl or heterocyclyl moiety by identical or different substituents, suitable aryl or heterocyclyl substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and, if appropriate, phenyl which is optionally monosubstituted to pentasubstituted by identical or different substituents from the series comprising halogen and/or straight-chain or branched alkyl having 1 to 4 carbon atoms;

and furthermore represents a carbonyl, sulphinyl or sulphonyl group, each of which is substituted, suitable substituents in each case being:

hydrogen, hydroxyl, amino, in each case straight-chain or branched alkyl, alkoxy, alkylamino or dialkylamino, each of which has 1 to 4 carbon atoms in the individual alkyl moieties, in each case straight-chain or branched halogenoalkyl or halogenoalkoxy, each of which has 1 to 4 carbon atoms and 1 to 9 identical or different halogen atoms, or aryl, aryloxy, arylamino or diarylamino, each of which has 6 or 10 carbon atoms in the individual aryl moieties and each of which is optionally monosubstituted to pentasubstituted in the aryl moiety, suitable substituents in the individual aryl moieties in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted to pentasubstituted by identical or different substituents from the series comprising halogen and/or straight-chain or branched alkyl having 1 to 4 carbon atoms;

and furthermore represents straight-chain or branched alkyl which has 1 to 6 carbon atoms and which is optionally monosubstituted to pentasubstituted by identical or different substituents, suitable substituents being:

fluorine, chlorine, bromine, iodine, hydroxyl, cyano, nitro, aminocarbonyl, formamido, in each case straight-chain or branched alkoxy, halogenoalkoxy, alkylthio, halogenoalkylthio, alkylamino, dialkylamino, alkanoyl, N-alkylaminocarbonyl, N,N-dialkylaminocarbonyl, alkanoylamido or alkylsulphonyl, each of which has 1 to 4 carbon atoms in the individual alkyl moieties and, if appropriate, 1 to 9 identical or different halogen atoms, or aryl, aryloxy, arylthio, arylamino, diarylamino, arylcarbonyl or arylsulphonyl, each of which has 6 or 10 carbon atoms in the individual aryl moieties or heterocyclyl which has 2 to 9 carbon atoms and 1 to 4 identical or different hetero atoms, in particular nitrogen, oxygen and/or sulphur, and each of these aryl, aryloxy, arylthio, arylamino, diarylamino, arylcarbonyl, arylsulphonyl or heterocyclyl is optionally monosubstituted to pentasubstituted in the aryl or heterocyclyl moiety, suitable aryl or heterocyclyl substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted to pentasubstituted by identical or different substituents from the series comprising halogen and/or straight-chain or branched alkyl having 1 to 4 carbon atoms;

and furthermore represents straight-chain or branched alkenyl which has 2 to 5 carbon atoms and which is optionally monosubstituted to trisubstituted by identical or different substituents, suitable substituents being:

fluorine, chlorine, bromine, iodine or cyano;

and furthermore represents straight-chain or branched alkinyl which has 2 to 5 carbon atoms and which is optionally monosubstituted to trisubstituted by identical or different substituents, suitable substituents being:

fluorine, chlorine, bromine or iodine;

and furthermore represents cycloalkyl or cycloalkenyl, each of which has 3 to 6 carbon atoms and each of which is optionally monosubstituted to pentasubstituted by identical or different substituents, suitable substituents, suitable substituents in each case being: fluorine, chlorine, bromine, iodine, and in each case straight-chain or branched alkyl or halogenoalkyl, each of which has 1 to 4 carbon atoms and, if appropriate, 1 to 9 identical or different halogen atoms;

and furthermore represents aryl which has 6 or 10 carbon atoms or heterocyclyl which has 2 to 9 carbon atoms and 1 to 4 identical or different hetero atoms, in particular nitrogen, oxygen and/or sulphur, and each of these aryl or heterocyclyl is optionally monosubstituted to pentasubstituted by identical or different substituents, suitable aryl or heterocyclyl substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted to pentasubstituted by identical or different substituents from the series comprising halogen and/or straight-chain or branched alkyl having 1 to 4 carbon atoms;

$R^2$ represents hydrogen, hydroxyl, fluorine, chlorine, bromine, iodine, straight-chain or branched alkyl having 1 to 4 carbon atoms or straight-chain or branched halogenoalkyl having 1 to 4 carbon atoms and 1 to 9 identical or different halogen atoms, $R^3$ represents hydrogen or an equivalent of an alkali metal cation, alkaline earth metal cation or an ammonium cation which is optionally monosubstituted to tetrasubstituted by identical or different substituents from the series comprising straight-chain or branched alkyl having 1 to 18 carbon atoms and/or benzyl, and furthermore represents straight-chain or branched alkyl which has 1 to 12 carbon atoms and which is optionally monosubstituted to pentasubstituted by identical or different substituents, suitable substituents being:

fluorine, chlorine, bromine, iodine, hydroxyl, cyano, nitro, aminocarbonyl, formamido, in each case straight-chain or branched alkoxy, halogenoalkoxy, alkylthio, halogenoalkylthio, alkylamino, dialkylamino, alkanoyl, N-alkylaminocarbonyl, N,N-dialkylaminocarbonyl, alkanoylamido or alkylsulphonyl, each of which has 1 to 8 carbon atoms in the individual alkyl moieties and, if appropriate, 1 to 17 identical or different halogen atoms, or aryl, aryloxy, arylthio, arylamino, diarylamino, arylcarbonyl or arylsulphonyl, each of which has 6 or 10 carbon atoms in the individual aryl moieties and each of which is optionally monosubstituted to pentasubstituted in the aryl moiety by identical or different substituents, or heterocyclyl having 2 to 9 carbon atoms and 1 to 4 identical or different hetero atoms, in particular nitrogen, oxygen and/or sulphur, which is optionally monosubstituted to pentasubstituted by identical or different substituents, suitable aryl or heterocyclyl substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted to pentasubstituted by identical or different substituents from the series comprising halogen and/or straight-chain or branched alkyl having 1 to 4 carbon atoms;

and furthermore represents straight-chain or branched alkenyl which has 2 to 5 carbon atoms and which is optionally monosubstituted to trisubstituted by identical or different substituents, suitable substituents being: fluorine, chlorine, bromine, iodine or cyano, or aryl which has 6 or 10 carbon atoms and which is optionally monosubstituted to trisubstituted by identical or different substituents, suitable substituents being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy, halogenoalkylthio, each of which has 1 to 4 carbon atoms and 1 to 9 identical or different halogen atoms;

and furthermore represents straight-chain or branched alkinyl which has 2 to 5 carbon atoms and which is optionally monosubstituted to trisubstituted by identical or different substituents, suitable substituents being: fluorine, chlorine, bromine or iodine;

and furthermore represents cycloalkyl or cycloalkenyl, each of which has 3 to 6 carbon atoms and each of which is optionally monosubstituted to pentasubstituted by identical or different substituents, suitable substituents in each case being:

fluorine, chlorine, bromine, iodine, and in each case straight-chain or branched alkyl or halogenoalkyl, each of which has 1 to 4 carbon atoms and, if appropriate, 1 to 9 identical or different halogen atoms;

and furthermore represents aryl which has 6 or 10 carbon atoms or heterocyclyl having 2 to 9 carbon atoms and 1 to 4 identical or different hetero atoms, in particular nitrogen, oxygen and/or sulphur, and each aryl or heterocyclyl is optionally monosubstituted to pentasubstituted by identical or different substituents, suitable aryl or heterocyclyl substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted to pentasubstituted by identical or different substituents from the series comprising halogen and/or straight-chain or branched alkyl having 1 to 4 carbon atoms;

$R^4$ and $R^5$ independently of each other in each case represent hydrogen, straight-chain or branched alkyl having 1 to 4 carbon atoms, straight-chain or branched halogenoalkyl having 1 to 4 carbon atoms and 1 to 9 identical or different halogen atoms, or cycloalkyl having 3 to 6 carbon atoms and X represents oxygen or sulphur.

Especially preferred compounds of the formula (I) are those in which $R^1$ represents hydrogen;

and furthermore represents in each case optionally substituted hydroxyl or mercaoto, suitable substituents in each case being:

straight-chain or branched alkyl having 1 to 4 carbon atoms, straight-chain or branched alkoxyalkyl, having in each case 1 to 4 carbon atoms in the individual alkyl moieties, straight-chain or branched dialkylaminoalkyl, having in each case 1 to 4 carbon atoms in the individual alkyl moieties, straight-chain or branched halogenoalkyl having 1 to 4 carbon atoms and 1 to 9 identical or different halogen atoms, or phenylalkyl which has 1 to 4 carbon atoms in the straight-chain or branched alkyl moiety or phenyl, pyridyl, pyridylmethyl, furanylmethyl, thienylmethyl, thiazolylmethyl or triazolylmethyl, and each of these phenylalkyl, phenyl, pyridyl, pyridylmethyl, furanylmethyl, thienylmethyl, thiazolylmethyl or triazolylmethyl is optionally monosubstituted to trisubstituted in the phenyl or heteroaryl moiety by identical or different substituents, suitable phenyl or heteroaryl substituents in each case being:

halogen, in each case straight-chain or branched alkyl, alkoxy or alkylthio, each o which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms;

and furthermore represents amino which is optionally monosubstituted or disubstituted by identical or different substituents, suitable substituents being: straight-chain or branched alkyl having 1 to 4 carbon atoms, allyl, propargyl, straight-chain or branched alkoxyalkyl having in each case 1 to 4 carbon atoms in the individual alkyl moieties, straight-chain or branched dialkylaminoalkyl having in each case 1 to 4 carbon atoms in the individual alkyl moieties, straight-chain or branched alkanoyl having 1 to 5 carbon atoms, straight-chain or branched alkoxycarbonyl having 2 to 5 carbon atoms, in each case straight-chain or branched alkylsulphinyl or alkylsulphonyl, each of which has 1 to 4 carbon atoms;

and furthermore represents a carbonyl, sulphinyl or sulphonyl group, each of which is substituted, suitable substituents in each case being: in each case straight-chain or branched alkyl, alkoxy, alkylamino or dialkylamino, each of which has 1 to 4 carbon atoms in the individual alkyl moieties;

and furthermore represents straight-chain or branched alkyl which has 1 to 6 carbon atoms and which is optionally monosubstituted to trisubstituted by identical or different substituents, suitable substituents being:

fluorine, chlorine, in each case straight-chain or branched alkoxy or alkylthio, each of which has 1 to 4 carbon atoms, in each case straight-chain or branched halogenoalkoxy or halogenoalkylthio, each of which has 1 to 4 carbon atoms and 1 to 9 identical or different halogen atoms, or phenyl which is optionally monosubstituted to trisubstituted by identical or different substituents, suitable substituents being:

halogen, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms;

and furthermore represents straight-chain or branched alkenyl having 3 to 6 carbon atoms;

and furthermore represents straight-chain or branched alkinyl having 2 to 6 carbon atoms;

and furthermore represents cyclopropyl which is optionally monosubstituted to trisubstituted by identical or different substituents from the series comprising methyl and/or chlorine;

and furthermore represents phenyl which is optionally monosubstituted to trisubstituted by identical or different substituents, suitable substituents in each case being:

halogen, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms;

and furthermore represents pyridyl, furanyl, tetrahydrofuranyl, thienyl or thiazolyl, each of which is optionally monosubstituted to trisubstituted by identical or different substituents, suitable substituents in each case being: in each case straight-chain or branched alkyl or alkoxy, each of which has 1 to 4 carbon atoms;

$R^2$ represents hydrogen or methyl, $R^3$ represents hydrogen or an equivalent of an alkali metal cation, alkaline earth metal cation or an ammonium cation which is optionally monosubstituted to tetrasubstituted by identical or different substituents from the series comprising straight-chain or branched alkyl having 1 to 18 carbon atoms and/or benzyl;

and furthermore represents straight-chain or branched alkyl which has 1 to 12 carbon atoms and which is optionally monosubstituted to trisubstituted by identical or different substituents, suitable substituents in each case being:

fluorine, chlorine, hydroxyl, cyano, in each case straight-chain or branched alkoxy, alkylthio, alkylamino, dialkylamino, alkanoyl, N-alkylaminocarbonyl, N,N-dialkylaminocarbonyl, alkanoylamido or alkylsulphonyl, each of which has 1 to 8 carbon atoms in the individual alkyl moieties, in each case straight-chain or branched halogenoalkoxy or halogenoalkylthio, each of which has 1 to 8 carbon atoms and 1 to 17 halogen atoms, and phenyl, phenoxy, phenylthio, phenylamino, phenylcarbonyl, phenylsulphonyl, pyridyl, furanyl, tetrahydrofuranyl, thienyl or thiazolyl, each of which is optionally monosubstituted to trisubstituted in the phenyl or heteroaryl moiety by identical or different substituents, suitable phenyl or heteroaryl substituents in each case being:

halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms;

and furthermore represents straight-chain or branched alkenyl having 2 to 6 carbon atoms;

and furthermore represents straight-chain or branched alkinyl having 2 to 6 carbon atoms;

and furthermore represents cyclopentyl or cyclohexyl, each of which is optionally monosubstituted to trisubstituted by identical or different substituents from the series comprising fluorine, chlorine and/or methyl;

and furthermore represents phenyl which is optionally monosubstituted to trisubstituted by identical or different substituents, suitable substituents in each case being:

halogen, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms;

and furthermore represents pyridyl, furanyl, tetrahydrofuranyl, thienyl or thiazolyl, each of which is optionally monosubstituted to trisubstituted by identical or different substituents, suitable substituents in each case being: in each case straight-chain or branched alkyl or alkoxy, each of which has 1 to 4 carbon atoms;

$R^4$ represents hydrogen, methyl or fluoromethyl, $R^5$ represents methyl, ethyl, n- or i-propyl or cyclopropyl and X represents oxygen or sulphur.

Very particularly preferred compounds of the formula (I) are those in which $R^1$ represents hydrogen, hydroxyl, methoxy, ethoxy, n- or i-propoxy, n-, i-, s- or t-butoxy, trifluoromethoxy, mercapto, methylthio, ethylthio, n- or i-propylthio, n-, i-, s- or t-butylthio, trifluoromethylthio, benzylthio, 2-pyridylthio, amino, N-methylamino, N-ethylamino, N-n-propylamino, N-i-propylamino, N,N-dimethylamino, N,N-diethylamino, N-methyl-N-ethylamino, methylcarbonylamino, ethylcarbonylamino, methoxycarbonylamino, ethoxycarbonylamino, methylsulphinyl, ethylsulphinyl, methylsulphonyl, ethylsulphonyl, methyl, ethyl, n- or i-propyl, n-, i-, s- or t-butyl, n- or i-pentyl, n- or i-hexyl, fluoromethyl, trifluoromethyl, methoxymethyl, ethoxymethyl, methylthiomethyl, ethylthiomethyl, allyl, ethinyl, propargyl, cyclopropyl or represents phenyl which is optionally monosubstituted or disubstituted by identical or different substituents, suitable substituents being:

fluorine, chlorine, bromine, methyl, ethyl, n- or i-propyl, n-, i-, s- or t-butyl, methoxy, ethoxy, n-or i-propoxy, n-, i-, s- or t-butoxy, methylthio, ethylthio, trifluoromethyl, trifluoromethoxy or trifluoromethylthio;

and furthermore represents pyridyl, furanyl, thienyl or thiazolyl, each of which is optionally monosubstituted or disubstituted by identical or different substituents, suitable substituents in each case being:

methyl, ethyl, n- or i-propyl, n-, i-, s- or t-butyl, methoxy, ethoxy, n- or i-propoxy, n-, i-, s-or t-butoxy, $R^2$ represents hydrogen, $R^3$ represents hydrogen, a sodium ion, potassium ion, calcium ion or an ammonium ion which is optionally monosubstituted to tetrasubstituted by identical or different substituents from the series comprising methyl, ethyl, n- or i-propyl, n-, i-, s- or t-butyl, n- or i-pentyl, n- or i-hexyl, n- or i-dodecyl and/or benzyl;

and furthermore represents methyl, ethyl, n- or i-propyl, n-, i-, s- or t-butyl, n- or i-pentyl, n- or i-hexyl, fluoromethyl, trifluoromethyl, hydroxyethyl, cyanoethyl, methoxyethyl, methylthioethyl, methylaminoethyl, ethylaminoethyl, N,N-dimethylaminoethyl, N,N-diethylaminoethyl, methylcarbonylmethyl, methylcarbonylethyl, N-methylaminocarbonylmethyl, N-methylaminocarbonylethyl, N-ethylaminocarbonylmethyl, N-ethylaminocarbonylethyl, N,N-dimethylaminocarbonylmethyl, N,N-diethylaminocarbonylmethyl,N,N-dimethylaminocarbonylethyl,N,N-diethylaminocarbonylethyl, N-acetylaminomethyl, N-acetylaminoethyl, N-propionylaminomethyl, N-propionylaminoethyl, methylsulphonylmethyl, methylsulphonylethyl, ethylsulphonylmethyl, ethylsulphonylethyl, allyl, propargyl, cyclopentyl, cyclohexyl or represents phenyl, pyridyl, benzyl or furanylmethyl, each of which is optionally monosubstituted to trisubstituted by identical or different substituents, suitable substituents in each case being:

fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy methylthio, ethylthio, trifluoromethyl, trifluoromethoxy or trifluoromethylthio, $R^4$ represents methyl, $R^5$ represents isopropyl and X represents oxygen.

The compounds of the general formula (I) which are mentioned in the Preparation Examples may be mentioned specifically.

If, for example, diethyl 2-methylpyrimidine-4,5-dicarboxylate and 2-amino-2,3-dimethylbutyramide are used as starting compounds, the course of the reaction of process (a) according to the invention can be represented by the following equation:

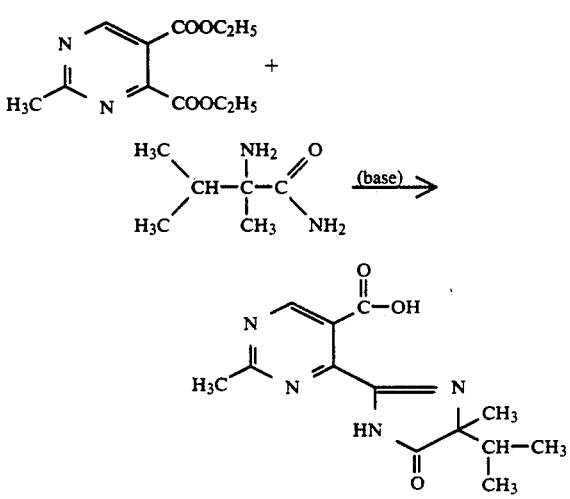

If, for example, 2-methyl-4-(4-methyl-4-isopropylimidazolin-5-on-2-yl)-pyrimidine-5-carboxylic acid and ethanol are used as starting substances and N,N'-dicyclohexylcarbodiimide as the condensing agent, then the course of the reaction of process (b) according to the invention can be represented by the following equation:

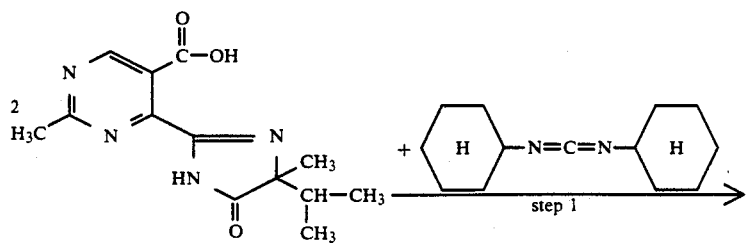

-continued

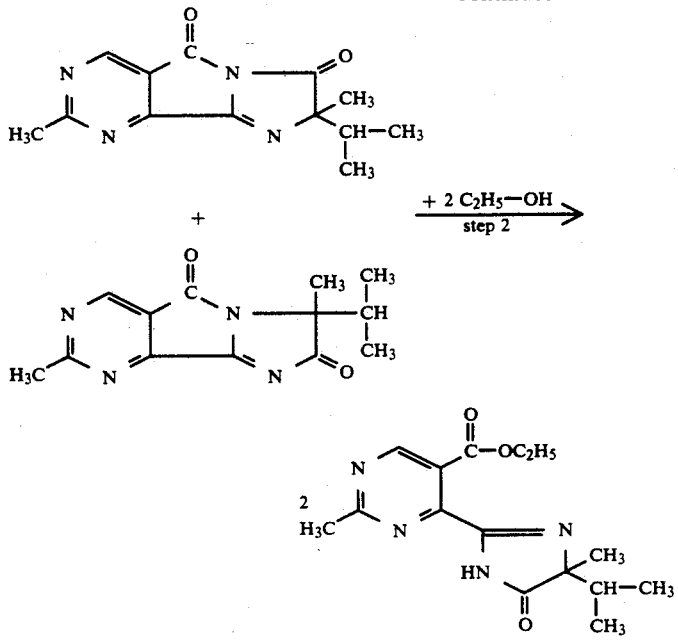

Formula (II) provides a general definition of the pyrimidine-4,5-dicarboxylates which are required as starting substances for carrying out process (a) according to the invention. In this formula (II), $R^1$ and $R^2$ preferably represent those radicals which have already been mentioned in connection with the description of the compounds of the formula (I) according to the invention as being preferred for these substituents. $R^6$ and $R^7$, independently of each other, preferably represent in each case straight-chain or branched alkyl having 1 to 4 carbon atoms, in particular methyl or ethyl.

The pyrimidine-4,5-dicarboxylates of the formula (II) are known or can be obtained analogously to known processes (compare, for example, EP 305,184; J. Chem. Soc., Perkin Trans. 1, 1980, 1667-1670; Justus Liebigs Ann. Chem. 1977, 1413-1420; J. Heterocycl. Chem. 14, 695-696 [1977]; Bull. Soc. Chim. Fr. 9-10 Pt. 2, 1543-1548, [1976]; Justus Liebigs Ann. Chem. 1976, 1809-1819; Chem. Ber. 108, 3877-3882 [1975]; Arch. Pharm. 308, 118-121 [1975]; JP 49024077; Justus Liebigs Ann. Chem. 1974, 1190-1194; DE 2,242,162; Chem. Pharm. Bull. 20, 1513-1521 [1972]; DE 2,046,577; J. Amer. Chem. Soc. 84, 837-844 [1962]; J. Heterocycl. Chem. 2, 202-204 [1965]; Chem. Pharm. Bull. 8, 262-264 [1960]; J. Org. Chem. 20, 1342-1346 [1955]; U.S. Pat. No. 2,774,760).

Formula (III) provides a general definition of the amino acid amides furthermore required as educts for carrying out process (a) according to the invention. In this formula (III), $R^4$ and $R^5$ preferably represent those radicals which have already been mentioned in connection with the description of the substances of the formula (I) according to the invention as being preferred for these substituents. The amino acid amides of the formula (III) are generally known or can be obtained analogously to generally known processes (compare, for example, Houben-Weyl-Müller "Methoden der organischen Chemie [Methods in Organic Chemistry]", Thieme Verlag Stuttgart 1974; Volume XV/1, p. 46 et seq.; Volume XV/2, p. 112 et seq.).

Formula (Ia) provides a general definition of the imidazolinylpyrimidinecarboxylic acids required as educts for carrying out process (b) according to the invention. In this formula (Ia), $R^1$, $R^2$, $R^4$ and $R^5$ preferably represent those radicals which have already been mentioned in connection with the description of the substances of the formula (I) according to the invention as being preferred for these substituents. The imidazolinylpyrimidinecarboxylic acids of the formula (Ia) are compounds according to the invention and can be obtained with the aid of process (a) according to the invention.

Formula (V) provides a general definition of the alcohols and thiols furthermore required as educts for carrying out process (b) according to the invention. In this formula (V), $R^3$ and X preferably represent those radicals which have already been mentioned in connection with the description of the substances of the formula (I) according to the invention as being preferred for these substituents. The alcohols and thiols of the formula (V) are generally known compounds of organic chemistry.

Suitable diluents for carrying out process (a) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers such as diethyl ether, diisopropyl ether, dioxane, tetrahydrofuran or ethylene glycol dimethyl ether or ethylene glycol diethyl ether, or amides such as N,N-dimethylformamide, N,N-dimethylacetamide, N-methylformanilide, N-methylpyrrolidone or hexamethylphosphoric triamide.

Process (a) according to the invention is preferably carried out in the presence of a suitable reaction auxiliary. Suitable reaction auxiliaries are all customary inorganic and organic bases. These include, for example, the hydrides, hydroxides, amides, alcoholates, acetates, carbonates or hydrogen carbonates of alkaline earth metals or alkali metals such as, for example, sodium hydride, sodium amide, sodium methylate, sodium ethylate, potassium tert.-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

When carrying out process (a) according to the invention, the reaction temperatures can be varied within a substantial range. In general, the process is carried out at temperatures between 0° C. and 180° C., preferably at temperatures between 20° C. and 120° C.

Process (a) according to the invention is customarily carried out under atmospheric pressure. However, it is also possible to carry out the process under increased or reduced pressure.

For carrying out process (a) according to the invention, 1.0 to 1.5 moles, preferably equimolar amounts, of amino acid amide of the formula (III) and 1.0 to 5.0 moles, preferably 1.0 to 3.0 moles, of base are generally employed as reaction auxiliaries per mole of pyrimidine-4,5-dicarboxylate of the formula (II).

The reaction is carried out and the reaction products are worked up and isolated by known processes (compare, in this context, for example EP 41,623 or the Preparation Examples).

Step 1 of process (b) according to the invention is carried out in the presence of a suitable condensing agent. Suitable condensing agents are all condensing agents which are customary for cyclisation reactions of this type. The following may be mentioned by way of example: acid halide formers, such as phosphorus tribromide, phosphorus pentachloride, phosphorus oxychloride or thionyl chloride, anhydride formers, such as ethyl chloroformate or methanesulphonyl chloride, carbodiimides, such as N,N,-dicyclohexylcarbodiimide (DCC), or other customary condensing agents, such as N,N'-carbonyldiimidazole, triphenylphosphine/carbon tetrachloride, or 2-ethoxy-N-ethoxycarbonyl-1,2-dihydroquinoline (EEDQ).

Suitable diluents for carrying out step 1 of process (b) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dioxane, tetrahydrofuran or ethylene glycol dimethyl ether or ethylene glycol diethyl ether; ketones such as acetone, butanone or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate; sulphoxides such as dimethyl sulphoxide, or alcohols, such as methanol, ethanol or isopropanol.

If appropriate, step 1 of process (b) according to the invention can be carried out in the presence of a suitable reaction auxiliary. Suitable reaction auxiliaries are all customary inorganic and organic bases. These include, for example, the hydrides, hydroxides, amides, alcoholates, acetates, carbonates or hydrogen carbonates of alkaline earth metals or alkali metals such as, for example, sodium hydride, sodium amide, sodium methylate, sodium ethylate, potassium tert.-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and also tertiary amines such as trimethylamine, triethylamine, tribtylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

When carrying out step 1 of process (b) according to the invention, the reaction temperatures can be varied within a substantial range. In general, the process is carried out at temperatures between −20° C. and 100° C., preferably at temperatures between 0° C. and 80° C.

For carrying out step 1 of process (b) according to the invention, 1.0 to 5.0 moles, preferably 1.0 to 1.5 moles, of condensing agent and, if appropriate, 0.001 to 2.0 moles, preferably 0.1 to 1.2 moles, of base are generally employed as reaction auxiliaries per mole of imidazolinylpyrimidine of the formula (Ia). The reaction is carried out and the reaction products are worked up and isolated by known processes (compare in this context, for example, EP 41,623 or the Preparation Examples).

Suitable diluents for carrying out step 2 of process (b) according to the invention are, again, inert organic solvents. The diluents mentioned in step 1 of process (b) according to the invention are preferably used. However, when liquid alcohols or thiols of the formula (V) are used as reaction component, it is also possible to use an appropriate excess of these simultaneously as the diluent. If appropriate, step 2 of process (b) according to the invention can be carried out in the presence of a suitable basic reaction auxiliary. Suitable reaction auxiliaries are all customary inorganic or organic bases. These include, for example, alkaline earth metal hydroxides or alkali metal hydroxides such as sodium hydroxide, calcium hydroxide, potassium hydroxide and also ammonium hydroxide, alkali metal carbonates such as sodium carbonate, potassium carbonate, potassium hydrogen carbonate, sodium hydrogen carbonate or ammonium carbonate, alkali metal acetates or alkaline earth metal acetates such as sodium acetate, potassium acetate, calcium acetate or ammonium acetate, and also tertiary amines such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

When carrying out step 2 of process (b) according to the invention, the reaction temperatures can be varied within a substantial range. In general, the process is carried out at temperatures between 0° C. and 150° C., preferably at temperatures between 20° C. and 100° C.

Step 2 of process (b) according to the invention is customarily carried out under atmospheric pressure.

For carrying out step 2 of process (b) according to the invention, 1.0 to 50 moles, preferably 1.0 to 10 moles, of alcohol or thiol of the formula (V) and, if approp- appropriate, 0.1 to 2.0 moles, preferably 0.5 to 1.2 moles, of base are generally employed as reaction auxiliaries per mole of imidazo-pyrrolo-pyrimidine of the formula (IVa) or (IVb).

The reaction is carried out and the reaction products are worked up and isolated by known processes (compare in this context, for example, EP 41,623 or the Preparation Examples).

In a particular embodiment, it is also possible to carry out steps 1 and 2 of process (b) according to the invention in one reaction step in a so-called "one-pot process". To this end, imidazolinylpyrimidines of the formula (Ia) are first introduced and then reacted in the "one-pot process" first with a condensing agent and subsequently with an alcohol or thiol of the formula (V).

The end products of the formula (I) are purified with the aid of customary processes, for example by column chromatography or by recrystallisation.

Compounds of the formula (I) according to the invention in which $R^3$ represents hydrogen can be converted into salts with the aid of customary methods, for example by dissolving them in a suitable inert solvent, subsequently adding a corresponding base, and isolating the salt by filtering off or by distilling off the solvent, and, if appropriate, purifying the product by washing with an inert solvent or by recrystallisation.

The compound of the formula (I) is characterised with the aid of the melting point or in the case of compounds which do not crystallise, with the aid of proton nuclear resonance spectroscopy ($^1$H NMR).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective combating of weeds in annual cultures.

In this context, the active compounds according to the invention can be employed with particular success for combating monocotyledon and dicotyledon weeds in monocotyledon and dicotyledon cultures such as, for example, wheat or soybeans. Besides, when used at appropriate dosage rates, the active compounds according to the invention also show leaf-acting insecticidal and fungicidal activities and can be employed, for example, for combating rice diseases such as, for example, against the pathogen causing rice blast disease (*Pyricularia oryzae*).

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose. Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%. For combating weeds, the active compounds according to the invention, as such or in the form of their formulations, can also be used as mixtures with known herbicides, finished formulations or tank mixes being possible.

Suitable herbicides for the mixtures are known herbicides, such as, for example, 1-amino-6-ethylthio-3-(2,2-dimethylpropyl)-1,3,5-triazine-2,4(1H,3H)-dione (AMETHYDIONE) or N-(2-benzothiazolyl)-N,N'-dimethyl-urea (METABENZTHIAZURON) for combating weeds in cereals; 4-amino-3-methyl-6-phenyl-1,2,4-triazin-5(4H)-one (METAMITRON) for combating weeds in sugar beet and 4-amino-6-(1,1-dimethylethyl)-3-methylthio-1,2,4-triazin-5(4H)-one (METRIBUZIN) for combating weeds in soy beans. Mixtures with 2,4-dichlorophenoxyacetic acid (2,4-D); 4-(2,4-dichlorophenoxy)-butyric acid (2,4-DB); 2,4-dichlorophenoxypropionic acid (2,4-DP); 5-(2-chloro-4-trifluoromethyl-phenoxy)-2-nitro-benzoic acid (ACIFLUORFEN); 2-chloro-2',6'-diethyl-N-methoxymethylacetanilide (ALACHLOR); methyl-6,6-dimethyl-2,4-dioxo-3-[1-(2-propenyloxyamino)-butylidene]-cyclohexanecarboxylic acid (ALLOXYDIM); 4-aminobenzenesulphonyl-methyl carbamate (ASULAM); 2-chloro-4-ethylamino-6-isopropylamino-1,3,5-triazine (ATRAZINE); methyl 2-[[[[[(4,6-dimethoxypyrimidin-2-yl)-amino]-carbonyl]-amino]-sulphonyl]-methyl]-benzoate (BENSULFURON); 3-isopropyl-2,1,3-benzothiadiazin-4-one 2,2-dioxide (BENTAZONE); methyl 5-(2,4-dichlorophenoxy)-2-nitrobenzoate (BIFENOX); 3,5-dibromo-4-hydroxybenzonitrile; (BROMOXYNIL); N-(butoxymethyl)-2-chloro-N-(2,6-diethyl-phenyl)-acetamide (BUTACHLOR); 5-amino-64-chloro-2-phenyl-2,3-dihydro-3-oxy-pyridazine (CHLORIDAZON); ethyl 2-{[(4-chloro-6-methoxy-2-pyrimidinyl)-aminocarbonyl]-aminosulphonyl}-benzoate (CHLORIMURON); N-(3-chlorophenyl)-isopropyl carbamate (CHLORPROPHAM); 2-chloro-N-{[(4-methoxy-6-methyl-1,3,5-triazin-2-yl)-amino]-carbonyl}-benzenesulphonamide (CHLORSULFURON); N,N-dimethyl-N,-(3-chloro-4-methylphenyl)-urea (CHLORTOLURON); exo-1-methyl-4-(1-methylethyl)-2-(2-methylphenyl-methoxy)-7-oxabicyclo-(2,2,1)-heptane (CINMETHYLIN); 3,6-dichloro-2-pyridinecarboxylic acid (CLOPYRALID); 2-chloro-4-ethylamino-6-(3-cyanopropylamino)-1,3,5-triazine (CYANAZINE); N,S-diethyl N-cyclohexyl-thiocarbamate(CYCLOATE);2-[1-(ethoximino)-butyl]-3-hydroxy-5-[tetrahydro-(2H)-thiopyran-3-yl]-2-cyclohexen-1-one (CYCLOXYDIM); 2-[4-(2,4-dichlorophenoxy)-phenoxy]-propionic acid, its methyl ester or its ethyl ester (DICLOFOP); 2-[(2-chlorophenyl)-methyl]-4,4-dimethylisoxazolidin-3-one (DIMETHAZONE); S-ethyl N,N-di-n-propyl-thiocarbamidate (EPTAME); 4-amino-6-t-butyl-3-ethylthio-1,2,4-triazin-5(4H)-one (ETHIOZIN); 2-{4-[(6-chloro-2-benzoxazolyl)-oxy]-phenoxy}-propanoic acid, its methyl ester or its ethyl ester (FENOXAPROP); 2-[4-(5-trifluoromethyl-2-pyridyloxy)-phenoxy]-propanoic acid or its butyl ester (FLUAZIFOP); N,N-dimethyl-N'-(3-trifluoromethyl-phenyl)-urea (FLUOMETURON); 1-methyl-3-phenyl-5-(3-trifluoromethylphenyl)-4-pyridone (FLURIDONE); [(4-amino-3,5-dichloro-6-fluoro-2-pyridinyl)-oy]-acetic acid or its 1-methylheptyl ester (FLUROXYPYR); 5-(2-chloro-4-trifluoromethyl-phenoxy)-N-methylsulphonyl-2-nitrobenzamide (FOMESAFEN); 2-{4-[(3-chloro-5-(trifluoromethyl)-2-pyridinyl)-oxy]-phenoxy}-propanoic acid or its ethyl ester (HALOXYFOP); 3-cyclohexyl-6-dimethylamino-1-methyl-1,3,5-triazine-2,4-dione (HEXAZINONE); methyl 2-[4,5-dihydro-4-methyl-4-(1-methylethyl)-5-oxo-1H-imidazol-2-yl]-4(5)-methylbenzoate (IMAZAMETHABENZ); 2-[5-methyl-5-(1-methylethyl)-4-oxo-2-imidazolin-2-yl]-3-quinolinecarboxylic acid (IMAQUIN); 2-[4,5-dihydro-4-methyl-4-isopropyl-5-oxo-(1H)-imidazol-2-yl]-5-ethylpyridine-3-carboxylic acid (IMAZETHAPYR); 3,5-diiodo-4-hydroxybenzonitrile (IOXYNIL); N,N-dimethyl-N'-(4-iso-propylphenyl)-urea (ISOPROTURON); 2-ethoxy-1-methyl-2-oxoethyl 5-[2-chloro-4-(trifluoromethyl)-phenoxy]-2-nitrobenzoate (LACTOFEN); (2-methyl-4-chlorophenoxy)-acetic acid (MCPA); (4-chloro-2-methylphenoxy)-propionic acid (MCPP); N-methyl-2-(1,3-benzothiazol-2-yloxy)-acetanilide (MEFENACET); 2-chloro-N-(2,6-dimethylphenyl)-N-[(1H)-pyrazol-1-yl-methyl]-acetamide (METAZACHLOR); 2-ethyl-6-methyl-N-(1-methyl-2-methoxyethyl)-chloroacetanilide (METOLACHLOR); 2-{[[((4-methyl-1,3,5-triazin-2-yl)-amino)-carbonyl]-amino-sulphonyl}-benzoic acid or its methyl ester (METSULFURON); S-ethyl N,N-hexamethylene-thiocarbamate (MOLINATE); 1-(3-trifluoromethyl-phenyl)-4-methylamino-5-chloro-6-pyridazone (NORFLURAZON); 4-(di-n-propylamino)-3,5-dinitrobenzenesulphonamide (ORYZALIN); 2-chloro-4-trifluoromethylphenyl 3-ethoxy-4-nitro-phenyl ether (OXYFLUORFEN); N-(1-ethylpropyl)-3,4-dimethyl-2,6-dinitroaniline (PENDIMETHALIN); 3-(ethoxycarbonylaminophenyl) N-(3'-methylphenyl)carbamate (PHENMEDIPHAM); α-chloro-2',6'-diethyl-N-(2-propoxyethyl)-acetanilide (PRETILACHLOR); 2-chloro-N-isopropylacetanilide (PROPACHLOR); isopropyl-N-phenyl-carbamate (PROPHAM); O-(6-chloro-3-phenyl-pyridazin-4-yl) S-octyl thiocarbonate (PYRIDATE); ethyl 2-[4-(6-chloro-quinoxalin-2-yl-oxy)-phenoxy]-propionate (QUIZALOFOPETHYL); 2-[1-(ethoxamino)-butylidene]-5-(2-ethylthiopropyl)-1,3-cyclohexadione (SETHOXYDIM); 2-chloro-4,6-bis-(ethylamino)-1,3,5-triazine (SIMAZINE); 2,4-bis-[N-ethylamino]-6-methylthio-1,3,5-triazine (SIMETRYNE); 4-ethylamino-2-t-butylamino-6-methylthio-s-triazine (TERBUTRYNE); methyl 3-[[[[(4-methoxy-6-methyl-1,3,5-triazin-2-yl)-amino]-carbonyl]-amino]-sulphonyl]-thiophene-2-carboxylate (THIAMETURON); S-[(4-chlorophenyl)-methyl]diethyl N,N-thiocarbamate (THIOBENCARB); S-(2,3,3-trichloroallyl) N,N-diisopropylthiocarbamate (TRIALLATE) or 2,6-dinitro-4-trifluoromethyl-N,N-dipropylaniline (TRIFLURALIN) may also be advantageous. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing. The amount of active compound used can vary within a substantial range. It depends essentially on the nature of the desired effect. In general, the amounts used are between 0.001 and 10 kg of active compound per hectare of soil surface, preferably between 0.005 and 5 kg per ha.

The preparation and use of the active compounds according to the invention can be seen from the following examples.

PREPARATION EXAMPLES

Example 1

(Process a)

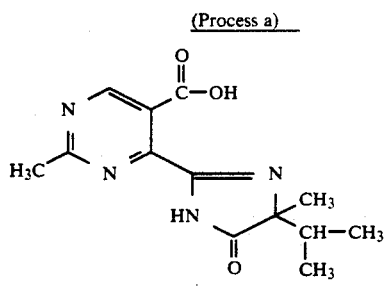

To a mixture of 98.8 g (0.415 mole) of diethyl 2-methylpyrimidine-4,5-dicarboxylate (compare, for example, J. Heterocycl. Chem. 2, 202–204 [1965]) and 54.0 g (0.415 mole) of 2-amino-2,3-dimethylbutyramide in 700 ml of anhydrous toluene there are added in portions 102.2 g (0.913 mole) of potassium tert.-butylate, and the mixture is subsequently stirred for 16 hours at 80° C. For working-up, the reaction mixture is cooled, the solid which has precipitated is filtered, washed several times with diethyl ether and subsequently dissolved in water. The aqueous solution is brought to pH 5 using half-concentrated hydrochloric acid, and the mixture is extracted five times using 200 ml portions of dichloromethane. The combined organic extracts are dried over sodium sulphate and concentrated in vacuo. The residue can be purified by chromatography on silica gel. 59 g (51% of theory) of 2-methyl-4-(4-methyl-4-isopropylimidazolin-5-on-2-yl)-pyrimidine-5carboxylic acid of melting point 56°–57° C. are obtained.

Example 2

Step 1 (IV-1)

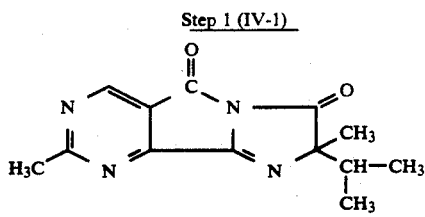

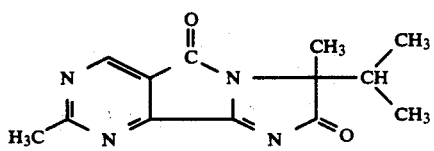

22.8 g (0.082 mole) of 2-methyl-4-(4-methyl-4-isopropylimidazolin-5-on-2-yl)-pyrimidine-5-carboxylic acid are suspended in 150 ml of tetrahydrofuran, the suspension is treated with 17.0 g (0.082 mole) of N,N'-dicyclohexylcarbodiimide, stirred for one hour at 40° C. and subsequently concentrated in vacuo, and the residue is purified by chromatography on silica gel (mobile phase: ethyl acetate/cyclohexane 1:1).

16.4 g (77% of theory) of an isomer mixture of the abovementioned imidazo-pyrrolo-pyrimidine are obtained as an oil.

$^1$H NMR (CDCl$_3$/tetramethylsilane): δ=0.95 (d,3H); 1.15 (d,3H); 1.58 (s,3H); 1.9 (m,1H); 3.02 (s,3H); 9.32 (s,1H) ppm.

Step 2

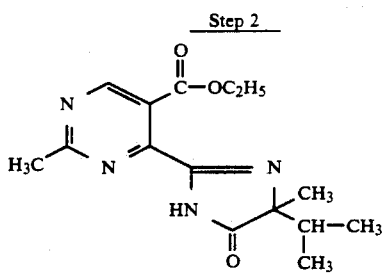

4.65 g (0.018 mole) of the imidazo-pyrrolo-pyrimidine mixture obtained in step 1 are treated with 20 ml of ethanol, and the mixture is stirred for 18 hours at room temperature. For working-up, excess ethanol is distilled off in vacuo, the residue is taken up in ethyl acetate and the mixture is washed several times with water, dried over sodium sulphate and concentrated in vacuo, and the residue is purified by chromatography on silica gel (mobile phase: ethyl acetate/n-hexane 3:1).

3.56 g (65% of theory) of ethyl 2-methyl-4-(4-methyl-4-isopropyl-imidazolin-5-on-2-yl)-pyrimidine-5-carboxylate are obtained as an oil.

$^1$H NMR (CDCl$_3$/tetramethylsilane): δ=0.87 (d,3H); 1.05 (d,3H); 1.37 (t,3H); 1.38 (s,3H); 2.09 (m,1H); 4.40 (m,2H); 8.86 (s,1H); 9.11 (s,1H) ppm.

The following imidazolinylpyrimidines of the general formula (I) are obtained in a corresponding manner and following the general preparation instructions:

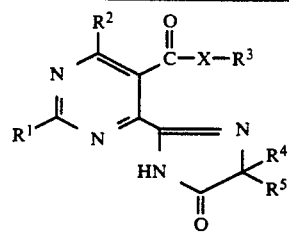
(I)

| Ex. No. | R¹ | R² | R³ | R⁴ | R⁵ | X | physical properties |
|---|---|---|---|---|---|---|---|
| 3 | i-C₃H₇ | H | H | CH₃ | i-C₃H₇ | O | m.p. 98–99° C. |
| 4 | H₃C—S— | H | H | CH₃ | i-C₃H₇ | O | m.p. 121–123° C. |
| 5 | t-C₄H₉ | H | H | CH₃ | i-C₃H₇ | O | m.p. 170–171° C. |
| 6 | H₅C₂—S— | H | H | CH₃ | i-C₃H₇ | O | m.p. 108–109° C. |
| 7 | H₅C₂—O— | H | H | CH₃ | i-C₃H₇ | O | m.p. 158–159° C. |
| 8 | (CH₃)₂N— | H | H | CH₃ | i-C₃H₇ | O | m.p. 178–179° C. |
| 9 | C₆H₅ | H | H | CH₃ | i-C₃H₇ | O | m.p. 205–206° C. |
| 10 | H | H | H | CH₃ | i-C₃H₇ | O | m.p. 210–211° C. |
| 11 | H₃C—NH— | H | H | CH₃ | i-C₃H₇ | O | m.p. 198–199° C. |
| 12 | H₅C₆—CH₂—S— | H | H | CH₃ | i-C₃H₇ | O | m.p. 187–188° C. |
| 13 | H₃C—O— | H | H | CH₃ | i-C₃H₇ | O | m.p. 140–141° C. |
| 14 | H₃C—S—CH₂— | H | H | CH₃ | i-C₃H₇ | O | m.p. 98–99° C. |
| 15 | CH₃ | H | K⊕ | CH₃ | i-C₃H₇ | O | m.p. 248–249° C. |
| 16 | H₃C—NH— | H | K⊕ | CH₃ | i-C₃H₇ | O | m.p. 238–239° C. |
| 17 | H₂N— | H | H | CH₃ | i-C₃H₇ | O | m.p. 191–192° C. |
| 18 | n-C₄H₉ | H | H | CH₃ | i-C₃H₇ | O | m.p. 102–103° C. |
| 19 | n-C₃H₇ | H | H | CH₃ | i-C₃H₇ | O | m.p. 102–103° C. |
| 20 | C₂H₅ | H | H | CH₃ | i-C₃H₇ | O | m.p. 127–128° C. |
| 21 | CH₃ | H | CH₃ | CH₃ | i-C₃H₇ | O | ¹H NMR*): 0,87; 1,06; 1,38; 2,09; 2,82; 3,91; 8,71; 8,85 |
| 22 | △ | H | H | CH₃ | i-C₃H₇ | O | m.p. 140–141° C. |
| 23 | CH₃—O—CH₂—/ C₂H₅—O—CH₂—(2:1) | H | H | CH₃ | i-C₃H₇ | O | ¹H-NMR*): 0,81(d); 0,98(d); 1,17(t); 1,26(s); 1,95(m); 3,42(s); 3,62(q); 4,72(s); 9,25(s) |
| 24 | CH₃ | H | —CH₂—C(CH₃)₃ | CH₃ | i-C₃H₇ | O | m.p. 84–85° C. |
| 25 | CH₃—O—C(O)—NH— | H | H | CH₃ | i-C₃H₇ | O | ¹H-NMR*): 0,83(d); 0,97(d); 1,2(s); 1,91(m); 3,7(s); 4,15(s); 9,12(s); 11,09(s) |
| 26 | CH₃ | H | —CH₂—C₆H₅ | CH₃ | i-C₃H₇ | O | m.p. 72° C. |
| 27 | CH₃ | H | —CH₂—C≡CH | CH₃ | i-C₃H₇ | O | m.p. 76–77° C. |
| 28 | CH₃ | H | —CH₂-(furan) | CH₃ | i-C₃H₇ | O | m.p. 44–45° C. |
| 29 | C₂H₅—O—CH₂— | H | H | CH₃ | i-C₃H₇ | O | ¹H-NMR*): 0,92(d); 1,14(d); 1,35(t); 1,54(s); 3,76(q); 4,89(s); 9,93(s) |
| 30 | CH₃ | H | Na⁺ | CH₃ | i-C₃H₇ | O | m.p. >260° C. |
| 31 | CF₃ | H | H | CH₃ | i-C₃H₇ | O | m.p. 164–165° C. |
| 32 | CH₃ | H | NH₄⁺ | CH₃ | i-C₃H₇ | O | m.p. >260° C. |
| 33 | CH₃ | H | ½ Ca²⁺ | CH₃ | i-C₃H₇ | O | m.p. >260° C. |
| 34 | H | H | C₂H₅ | CH₃ | i-C₃H₇ | O | m.p. 58–59° C. |
| 35 | CH₃ | H | n-C₃H₇ | CH₃ | i-C₃H₇ | O | m.p. 84–85° C. |
| 36 | 2-pyridyl | H | H | CH₃ | i-C₃H₇ | O | m.p. 206–207° C. |
| 37 | 2-thienyl | H | H | CH₃ | i-C₃H₇ | O | m.p. 212–213° C. |

-continued

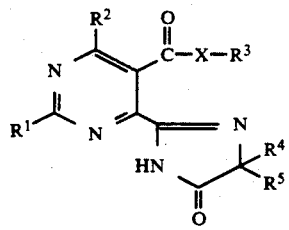
(I)

| Ex. No. | R¹ | R² | R³ | R⁴ | R⁵ | X | physical properties |
|---|---|---|---|---|---|---|---|
| 38 | (3-pyridyl) | H | H | CH₃ | i-C₃H₇ | O | m.p. 242–243° C. |
| 39 | CH₃ | H | i-C₃H₇ | CH₃ | i-C₃H₇ | O | m.p. 98–99° C. |
| 40 | CH₃ | H | —CH₂—CH=CH₂ | CH₃ | i-C₃H₇ | O | m.p. 78–79° C. |
| 41 | CH₃ | H | n-C₄H₉ | CH₃ | i-C₃H₇ | O | m.p. 88–89° C. |
| 42 | (2-furyl) | H | H | CH₃ | i-C₃H₇ | O | m.p. 239–240° C. |
| 43 | C₆H₅—CH₂— | H | H | CH₃ | i-C₃H₇ | O | m.p. 147° C. |
| 44 | H | H | CH₃ | CH₃ | i-C₃H₇ | O | m.p. 92–93° C. |
| 45 | H | H | —CH₂—C₆H₅ | CH₃ | i-C₃H₇ | O | ¹H-NMR*): 0,86(d); 1,30(d); 1,36(s); 2,07(m); 5,38(m); 7,38(m); 8,74(s); 8,94(s); 9,33(s); |
| 46 | H | H | n-C₄H₉ | CH₃ | i-C₃H₇ | O | m.p. 63–64° C. |
| 47 | H | H | —CH₂—CH=CH₂ | CH₃ | i-C₃H₇ | O | m.p. 124–125° C. |
| 48 | H | H | —CH₂—C≡CH | CH₃ | i-C₃H₇ | O | ¹H-NMR*): 0,87(d); 1,06(d); 1,4(s); 2,11(m); 2,56(t); 4,93(d); 8,94(s); 8,97(s); 9,37(s) |
| 49 | H | H | n-C₃H₇ | CH₃ | i-C₃H₇ | O | m.p. 90–91° C. |
| 50 | H | H | —CH₂—C(CH₃)₃ | CH₃ | i-C₃H₇ | O | m.p. 98–99° C. |
| 51 | C₂H₅ | H | CH₃ | CH₃ | i-C₃H₇ | O | m.p. 124–125° C. |
| 52 | C₂H₅ | H | C₂H₅ | CH₃ | i-C₃H₇ | O | m.p. 105–106° C. |
| 53 | C₂H₅ | H | n-C₃H₇ | CH₃ | i-C₃H₇ | O | m.p. 98–99° C. |
| 54 | C₂H₅ | H | i-C₃H₇ | CH₃ | i-C₃H₇ | O | m.p. 137–138° C. |
| 55 | C₂H₅ | H | n-C₄H₉ | CH₃ | i-C₃H₇ | O | m.p. 128–129° C. |
| 56 | C₂H₅ | H | —CH₂—C₆H₅ | CH₃ | i-C₃H₇ | O | m.p. 102–103° C. |
| 57 | C₂H₅ | H | —CH₂—CF₃ | CH₃ | i-C₃H₇ | O | m.p. 145–146° C. |
| 58 | C₂H₅ | H | —CH₂—CH=CH₂ | CH₃ | i-C₃H₇ | O | m.p. 109–110° C. |
| 59 | C₂H₅ | H | —CH₂—C≡CH | CH₃ | i-C₃H₇ | O | m.p. 138–139° C. |
| 60 | C₂H₅ | H | s-C₄H₉ | CH₃ | i-C₃H₇ | O | m.p. 98–99° C. |
| 61 | C₂H₅ | H | cyclopentyl | CH₃ | i-C₃H₇ | O | m.p. 148–149° C. |
| 62 | NH₂ | H | n-C₃H₇ | CH₃ | i-C₃H₇ | O | m.p. 130–131° C. |
| 63 | NH₂ | H | —CH₂—C₆H₅ | CH₃ | i-C₃H₇ | O | ¹H-NMR*): 0,88(d); 1,02(d); 1,33(s); 2,06(m); 5,31(m); 5,49(s); 7,36(m); 8,55(s); 8,68(s) |
| 64 | C₂H₅ | H | cyclohexyl | CH₃ | i-C₃H₇ | O | m.p. 84–85° C. |
| 65 | C₂H₅ | H | —CH₂—CH₂—S—CH₃ | CH₃ | i-C₃H₇ | O | m.p. 93–94° C. |
| 66 | C₂H₅ | H | —CH₂—CH₂—NH—CH₃ | CH₃ | i-C₃H₇ | O | m.p. 91–92° C. |
| 67 | C₂H₅ | H | —CH₂—C(O)—CH₃ | CH₃ | i-C₃H₇ | O | m.p. 93–94° C. |
| 68 | n-C₃H₇ | H | CH₃ | CH₃ | i-C₃H₇ | O | m.p. 43–44° C. |
| 69 | n-C₃H₇ | H | C₂H₅ | CH₃ | i-C₃H₇ | O | m.p. 81–82° C. |
| 70 | n-C₃H₇ | H | n-C₃H₇ | CH₃ | i-C₃H₇ | O | m.p. 84–85° C. |
| 71 | n-C₃H₇ | H | —CH₂—C≡CH | CH₃ | i-C₃H₇ | O | m.p. 88–89° C. |
| 72 | CH₃ | H | —CH₂—CF₃ | CH₃ | i-C₃H₇ | O | m.p. 128–129° C. |
| 73 | CH₃ | H | —CH₂—C(O)—CH₃ | CH₃ | i-C₃H₇ | O | ¹H-NMR*): 0,85(d); 1,03(d); 1,36(s); 2,07(m); 2,25(s); 2,83(s); |

-continued

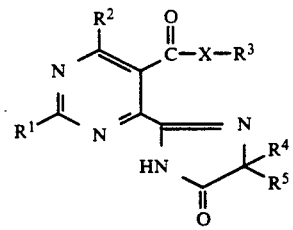

(I)

| Ex. No. | R¹ | R² | R³ | R⁴ | R⁵ | X | physical properties |
|---|---|---|---|---|---|---|---|
| 74 | $C_2H_5-S-$ | H | $CH_3$ | $CH_3$ | $i-C_3H_7$ | O | 4,88(m); 8,84(s); 8,99(s) m.p. 88–89° C. |
| 75 | $C_2H_5-S-$ | H | $C_2H_5$ | $CH_3$ | $i-C_3H_7$ | O | m.p. 104–105° C. |
| 76 | $C_2H_5$ | H | $-CH_2-CH_2-NH_2$ | $CH_3$ | $i-C_3H_7$ | O | m.p. 135–136° C. |
| 77 | $C_2H_5$ | H | $-CH_2-\text{furyl}$ | $CH_3$ | $i-C_3H_7$ | O | m.p. 109–110° C. |
| 78 | cyclopropyl | H | $CH_3$ | $CH_3$ | $i-C_3H_7$ | O | m.p. 130–131° C. |
| 79 | cyclopropyl | H | $n-C_3H_7$ | $CH_3$ | $i-C_3H_7$ | O | m.p. 110–111° C. |
| 80 | cyclopropyl | H | $i-C_3H_7$ | $CH_3$ | $i-C_3H_7$ | O | m.p. 126–127° C. |
| 81 | cyclopropyl | H | $-CH_2-CH=CH_2$ | $CH_3$ | $i-C_3H_7$ | O | m.p. 128–129° C. |
| 82 | $n-C_4H_9$ | H | $CH_3$ | $CH_3$ | $i-C_3H_7$ | O | ¹H-NMR*): 0,87(d); 0,97(t); 1,06(d); 1,42(m); 1,83(m); 2,09(m); 3,04(m); 3,92(s); 8,74(s); 8,85(s) |
| 83 | $n-C_4H_9$ | H | $C_2H_5$ | $CH_3$ | $i-C_3H_7$ | O | m.p. 68–69° C. |
| 84 | $n-C_4H_9$ | H | $n-C_3H_7$ | $CH_3$ | $i-C_3H_7$ | O | m.p. 70–71° C. |
| 85 | $i-C_3H_7$ | H | $CH_3$ | $CH_3$ | $i-C_3H_7$ | O | m.p. 84–85° C. |
| 86 | $i-C_3H_7$ | H | $C_2H_5$ | $CH_3$ | $i-C_3H_7$ | O | m.p. 115–116° C. |
| 87 | $i-C_3H_7$ | H | $-CH_2-CH=CH_2$ | $CH_3$ | $i-C_3H_7$ | O | m.p. 120–121° C. |
| 88 | $CH_3-O-$ | H | $CH_3$ | $CH_3$ | $i-C_3H_7$ | O | m.p. 132–133° C. |
| 89 | 2-pyridyl | H | $CH_3$ | $CH_3$ | $i-C_3H_7$ | O | ¹H-NMR*): 0,88(d); 1,08(d); 1,39(s); 2,1(m); 7,51(m); 7,95(m); 8,62(m); 8,8(m); 9,07(s) |
| 90 | 2-pyridyl | H | $C_2H_5$ | $CH_3$ | $i-C_3H_7$ | O | m.p. 104–105° C. |
| 91 | 2-pyridyl | H | $-CH_2-CH=CH_2$ | $CH_3$ | $i-C_3H_7$ | O | m.p. 78–79° C. |
| 92 | 2-pyridyl | H | $-CH_2-C\equiv CH$ | $CH_3$ | $i-C_3H_7$ | O | m.p. 156–157° C. |
| 93 | 2-pyridyl | H | $n-C_3H_7$ | $CH_3$ | $i-C_3H_7$ | O | ¹H-NMR*): 0,88(d); 1,01(t); 1,07(d); 1,4(s); 1,75(m); 2,11(m); 4,3(m); 7,4(m); 7,78(m); 8,9(m); 9,03(s); 9,09(m) |

-continued

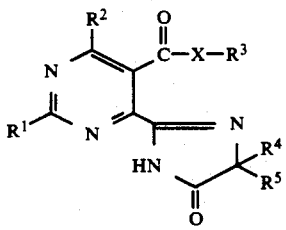

(I)

| Ex. No. | R¹ | R² | R³ | R⁴ | R⁵ | X | physical properties |
|---|---|---|---|---|---|---|---|
| 94 | 3-pyridyl | H | —CH₂—CH=CH₂ | CH₃ | i-C₃H₇ | O | ¹H-NMR*): 0,9(d); 1,03(d); 1,4(s); 2,08(m); 3,81(m); 4,85(m); 5,39(m); 6,01(m); 7,75(m); 8,91(m); 9,0(m); 9,05(m); 10,0(m) |
| 95 | 3-pyridyl | H | —CH₂—C≡CH | CH₃ | i-C₃H₇ | O | ¹H-NMR*): 0,9(d); 1,08(d); 1,43(s); 2,11(m); 2,56(m); 4,95(m); 7,51(m); 8,72(m); 8,77(m); 9,01(s); 9,69(m) |
| 96 | C₂H₅ | H | n-C₆H₁₃ | CH₃ | i-C₃H₇ | O | m.p. 87–88° C. |
| 97 | C₂H₅ | H | —CH₂—CH₂—O—CH₃ | CH₃ | i-C₃H₇ | O | m.p. 83–84° C. |
| 98 | C₂H₅ | H | —CH₂—CH₂—CH(CH₃)₂ | CH₃ | i-C₃H₇ | O | m.p. 90–91° C. |
| 99 | 2-thienyl | H | —CH₂—CH₂—CH(CH₃)₂ | CH₃ | i-C₃H₇ | O | m.p. 131–132° C. |
| 100 | 2-thienyl | H | —CH₂—C≡CH | CH₃ | i-C₃H₇ | O | m.p. 158–159° C. |
| 101 | 2-thienyl | H | —CH₂—C(O)—CH₃ | CH₃ | i-C₃H₇ | O | m.p. 133–134° C. |
| 102 | 2-thienyl | H | n-C₆H₁₃ | CH₃ | i-C₃H₇ | O | m.p. 98–99° C. |
| 103 | C₂H₅—O—CH₂— | H | CH₃ | CH₃ | i-C₃H₇ | O | — |
| 104 | C₆H₅ | H | C₂H₅ | CH₃ | i-C₃H₇ | O | m.p. 123–124° C. |
| 105 | C₆H₅ | H | i-C₃H₇ | CH₃ | i-C₃H₇ | O | m.p. 155–156° C. |
| 106 | C₆H₅ | H | —CH₂—CH₂CH(CH₃)₂ | CH₃ | i-C₃H₇ | O | m.p. 168–169° C. |
| 107 | C₆H₅—CH₂— | H | n-C₄H₉ | CH₃ | i-C₃H₇ | O | ¹H-NMR*): 0,77(d); 0,88(t); 0,96(d); 1,21(s); 1,31(m); 1,62(m); 1,91(m); 4,22(m); 4,32(m); 7,3(m); 9,1(s); 11,59(s) |
| 108 | C₆H₅—CH₂— | H | —CH₂—CH=CH₂ | CH₃ | i-C₃H₇ | O | m.p. 44–45° C. |
| 109 | 2-furyl | H | —CH₂—C(O)—CH₃ | CH₃ | i-C₃H₇ | O | m.p. 64–65° C. |
| 110 | 2-furyl | H | —CH₂—CF₃ | CH₃ | i-C₃H₇ | O | m.p. 174–175° C. |
| 111 | C₆H₅—S—CH₂— | H | —CH₂—CH=CH₂ | CH₃ | i-C₃H₇ | O | ¹H-NMR*): 0,84(d); 1,1(d); 1,34(s); 2,05(m); 4,42(m); 4,5(m); 4,75(m); 5,32(m); 5,95(m); 7,3(m); 8,5(s); 8,71(s) |
| 112 | C₆H₅—S—CH₂— | H | —CH₂—C≡CH | CH₃ | i-C₃H₇ | O | ¹H-NMR*): 0,85(d); 1,02(d); 1,35(s); 2,02(m); 4,52(m); 4,45(s); |

-continued

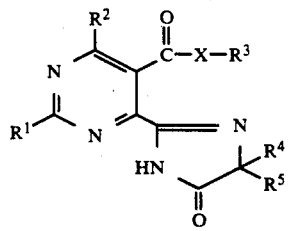

| Ex. No. | $R^1$ | $R^2$ | $R^3$ | $R^4$ | $R^5$ | X | physical properties |
|---|---|---|---|---|---|---|---|
|  |  |  |  |  |  |  | 4,87(m); 7,35(m); 8,68(s); 8,75(s) |
| 113 | $C_6H_5-S-CH_2-$ | H | $-CH_2-C(O)-CH_3$ | $CH_3$ | $i-C_3H_7$ | O | m.p. 84–85° C. |
| 114 | $C_6H_5-S-CH_2-$ | H | $-CH_2-C_6H_5$ | $CH_3$ | $i-C_3H_7$ | O | m.p. 78–79° C. |
| 115 | $C_2H_5-O-$ | H | $CH_3$ | $CH_3$ | $i-C_3H_7$ | O | m.p. 115–116° C. |
| 116 | $C_6H_5-S-CH_2-$ | H | $n-C_6H_{13}$ | $CH_3$ | $i-C_3H_7$ | O | m.p. 58–59° C. |
| 117 | $C_6H_5-S-CH_2-$ | H | $-CH_2-CF_3$ | $CH_3$ | $i-C_3H_7$ | O | m.p. 74–75° C. |
| 118 | $C_2H_5-O-$ | H | $C_2H_5$ | $CH_3$ | $i-C_3H_7$ | O | m.p. 88–89° C. |
| 119 | $C_2H_5$ | H | $-CH_2-CH_2-CN$ | $CH_3$ | $i-C_3H_7$ | O | m.p. 140–141° C. |
| 120 | $C_2H_5$ | H | $-CH(CH_3)-CN$ | $CH_3$ | $i-C_3H_7$ | O | m.p. 130–111° C. |
| 121 | $C_2H_5$ | H | $-CH_2-CN$ | $CH_3$ | $i-C_3H_7$ | O | m.p. 118–119° C. |

*)The $^1$H NMR spectra were recorded in deuterochloroform ($CDCl_3$) or hexadeuterodimethyl sulphoxide ($DMSO-d_6$) with tetramethylsilane (TMS) as the internal standard. The data given is the chemical shift as δ value in ppm.

TABLE 2

| Bsp.Nr. | $R^1$ | $R^2$ | $R^4$ | $R^5$ | physical properties |
|---|---|---|---|---|---|
| IV-2 | H | H | $CH_3$ | $i-C_3H_7$ | $^1$H-NMR*): 1,17(m); 1,56(s); 2,24(m); 9,15(s); 9,44(s) |
| IV-3 | $C_2H_5$ | H | $CH_3$ | $i-C_3H_7$ | m.p. 101–102° C. |

*)The $^1$H NMR spectra were recorded in deuterochloroform ($CDCl_3$) or hexadeuterodimethyl sulphoxide ($DMSO-d_6$) with tetramethylsilane (TMS) as the internal standard. The data given is the chemical shift as δ value in ppm.

Use Examples

In the Use Examples which follow, the compound listed below was employed as comparison substance:

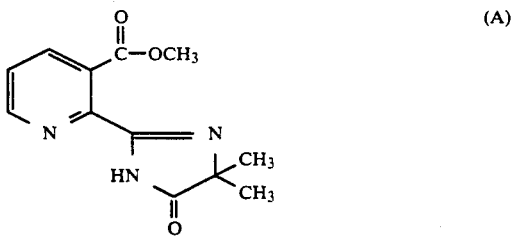

(A)

Methyl 2-(4,4-dimethylimidazolin-5-on-2-yl)-pyridine-3-carboxylate (disclosed in EP 41,623)

Example A

Pre-emergence test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison with the development of the untreated control. The figures denote:

0%=no action (like untreated control)

100%=total destruction

A clearly superior activity and a clearly superior crop plant selectivity compared with the prior art is shown in this test, for example by the compounds of the following preparation examples 1 and 3.

Example B

Post-emergence test

| Solvent: | 5 parts by weight of acetone |
|---|---|
| Emulsifier: | 1 part by weight of alkylaryl polyglycol ether |

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area.

After three weeks, the degree of damage to the plants is rated in % damage in comparison with the development of the untreated control. The figures denote:

0%=no action (like untreated control)

100%=total destruction

A clearly superior activity and a clearly superior crop plant selectivity compared with the prior art is shown in this test, for example by the compounds of the following Preparation Examples: 1, 4, 7 and 10.

It will be understood that the specification and examples are illustrative but not limitative of the present invention and that other embodiments within the spirit and scope of the invention will suggest themselves to those skilled in the art.

We claim:

1. A substituted imidazolinylpyrimidine of the formula

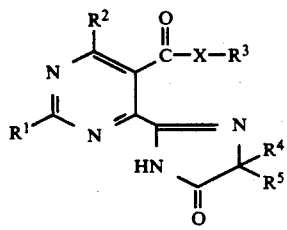

in which

R$^1$ represents hydrogen, fluorine, chlorine, bromine, iodine, cyano, nitro or thiocyanato;

and furthermore represents hydroxy, mercapto, straight-chain or branched alkyloxy or alkylmercapto having 1 to 8 carbon atoms, straight-chain or branched halogenoalkyloxy, or halogenoalkylmercapto having 1 to 8 carbon atoms and 1 to 17 identical or different halogen atoms, straight-chain or branched alkoxyalkyloxy or alkoxyalkylmercapto having in each case 1 to 8 carbon atoms in the individual alkyl moieties, straight-chain or branched dialkylaminoalkyloxy or dialkylaminoalkylmercapto having in each case 1 to 8 carbon atoms in the individual alkyl moieties, straight-chain or branched alkanoyloxy or alkanoylthio having 1 to 9 carbon atoms, straight-chain or branched alkoxycarbonyloxy or alkoxycarbonylthio having 2 to 9 carbon atoms, straight-chain or branched alkylsulphonyloxy or alkylsulphonylthio having 1 to 8 carbon atoms, straight-chain or branched alkoxysulphonyloxy or alkoxysulphonylthio having 1 to 8 carbon atoms, or arylalkyloxy or arylalkylthio which has 1 to 8 carbon atoms in the straight-chain or branched alkyl moiety and 6 to 10 carbon atoms in the aryl moiety, aryloxy or arylthio having 6 to 10 carbon atoms, arylcarbonyloxy or arylcarbonylthio, arylsulphonyloxy, arylsulphonylthio, aryloxysulphonyloxy or aryloxysulphonylthio having in each case 6 to 10 carbon atoms in the aryl moiety, heterocyclyloxy or heterocyclylthio or heterocyclylalkyloxy or heterocyclylalkylthio having, if present, 1 to 4 carbon atoms in the straight-chain or branched alkyl moiety, and each of these arylalkyl, aryl, arylcarbonyl, arylsulphonyl, aryloxysulphonyl, heterocyclyl or heterocyclylalkyl moieties is optionally monosubstituted or polysubstituted in the aryl or heterocyclyl moiety by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkyloxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and also phenyl which is optionally monosubstituted or polysubstituted by identical or different substituents selected from the group consisting of halogen and straight-chain or branched alkyl having 1 to 4 carbon atoms;

or R$^1$ represents amino which is optionally monosubstituted or disubstituted by identical or different substituents selected from the group consisting of straight-chain or branched alkyl having 1 to 8 carbon atoms, straight-chain or branched alkenyl having 2 to 8 carbon atoms, straight-chain or branched alkinyl having 2 to 8 carbon atoms, straight-chain or branched halogenoalkyl having 1 to 8 carbon atoms and 1 to 17 identical or different halogen atoms, straight-chain or branched alkoxyalkyl having in each case 1 to 8 carbon atoms in the individual alkyl moieties, straight-chain or branched dialkylaminoalkyl, having in each case 1 to 8 carbon atoms in the individual alkyl moieties, straight-chain or branched alkanoyl having 1 to 9 carbon atoms, straight-chain or branched alkoxycarbonyl having 2 to 9 carbon atoms, straight-chain or branched alkylsulphonyl having 1 to 8 carbon atoms, straight-chain or branched alkoxysulphonyl having 1 to 8 carbon atoms, straight-chain or branched dialkylaminosulphonyl having in each case 1 to 8 carbon atoms in the individual alkyl moieties, or arylalkyl which has 1 to 8 carbon atoms in the straight-chain or branched alkyl moiety and 6 to 10 in the aryl moiety, aryl having 6 to 10 carbon atoms, arylcarbonyl, arylsulphonyl or aryloxysulphonyl, each of which has 6 to 10 carbon atoms in the aryl moiety, heterocyclyl or heterocyclylalkyl, each of which has, if present, 1 to 4 carbon atoms in the straight-chain or branched alkyl moiety and each of these arylalkyl, aryl, arylcarbonyl, arysulphonyl, aryoxysulphonyl, heterocyclyl or heterocyclylalkyl is optionally monosubstituted or polysubstituted in the aryl or heterocyclyl moiety by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and, if present, phenyl which is optionally monosubstituted or polysubstituted by identical or different substituents selected from the group consisting of halogen and straight-chain or branched alkyl having 1 to 4 carbon atoms;

or R$^1$ represents carbonyl, sulphinyl or sulphonyl group, each of which is substituted by a member selected from the group consisting of hydrogen, hydroxyl, amino, in each case straight-chain or branched alkyl, alkoxy, alkylamino or dialkylamino, each of which has 1 to 8 carbon atoms in the individual alkyl moieties, in each case straight-chain or branched halogenoalkyl or halogenoalkoxy, each of which has 1 to 8 carbon atoms and 1 to 17 identical or different halogen atoms, or aryl, aryloxy, arylamino or diarylamino, each of which has 6 to 10 carbon atoms in the individual aryl moieties and each of which is optionally monosubstituted or polysubstituted in the aryl moiety by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents selected from the group consisting of halogen and straight-chain or branched alkyl having 1 to 4 carbon atoms;

or $R^1$ represents straight-chain or branched alkyl which has 1 to 8 carbon atoms and which is optionally monosubstituted or polysubstituted by identical or different substituents selected from the group consisting of fluorine, chlorine, bromine, iodine, hydroxyl, cyano, nitro, aminocarbonyl, formamido, in each case straight-chain or branched alkoxy, halogenoalkoxy, alkylthio, halogenoalkylthio, alkylamino, dialkylamino, alkanoyl, N-alkylaminocarbonyl, N,N-dialkylaminocarbonyl, alkanoylamido or alkylsulphonyl, each of which has 1 to 8 carbon atoms in the individual alkyl moieties and, if present, 1 to 17 identical or different halogen atoms, or aryl, aryloxy, arylthio, arylamino, diarylamino, arylcarbonyl or arylsulphonyl, each of which has 6 to 10 carbon atoms in the individual aryl moieties and each of which is optionally monosubstituted or polysubstituted in the aryl moiety by identical or different substituents, or heterocyclyl which is optionally monosubstituted or polysubstituted by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents selected from the group consisting of halogen and straight-chain or branched alkyl having 1 to 4 carbon atoms;

or $R^1$ represents straight-chain or branched alkenyl which has 2 to 8 carbon atoms and which is optionally monosubstituted or polysubstituted by identical or different substituents, selected from the group consisting of fluorine, chlorine, bromine, iodine or cyano; or $R^1$ represents straight-chain or branched alkynyl which has 2 to 8 carbon atoms and which is optionally monosubstituted or polysubstituted by identical or different substituents selected from the group consisting of fluorine, chlorine, bromine and iodine;

or $R^1$ represents cycloalkyl or cycloalkenyl, each of which has 3 to 8 carbon atoms and each of which is optionally monosubstituted or polysubstituted by identical or different substituents selected from the group consisting of fluorine, chlorine, bromine, iodine, and in each case straight-chain or branched alkyl or halogenoalkyl, each of which has 1 to 8 carbon atoms and, if present, 1 to 17 identical or different halogen atoms;

or $R^1$ represents aryl which has 6 to 10 carbon atoms or heterocyclyl, and each aryl or heterocyclyl is optionally monosubstituted or polysubstituted by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents selected from the group consisting of halogen and/or straight-chain or branched alkyl having 1 to 4 carbon atoms;

$R^2$ represents hydrogen, hydroxyl, fluorine, chlorine, bromine, iodine, straight-chain or branched alkyl having 1 to 8 carbon atoms or straight-chain or branched halogenoalkyl having 1 to 8 carbon atoms and 1 to 17 identical or different halogen atoms, $R^3$ represents hydrogen or an equivalent of an alkali metal cation, alkaline earth metal cation or an ammonium cation which is optionally monosubstituted or polysubstituted by identical or different substituents selected from the group consisting of straight-chain or branched alkyl having 1 to 18 carbon atoms and/or benzyl, or $R^3$ represents straight-chain or branched alkyl which has 1 to 18 carbon atoms and which is optionally monosubstituted or polysubstituted by identical or different substituents selected from the group consisting of fluorine, chlorine, bromine, iodine, hydroxyl, cyano, nitro, aminocarbonyl, formamido, in each case straight-chain or branched alkoxy, halogenoalkoxy, alkylthio, halogenoalkylthio, alkylamino, dialkylamino, alkanoyl, N-alkylamino-carbonyl, N,N-dialkylaminocarbonyl, alkanoylamido or alkylsulphonyl, each of which has 1 to 8 carbon atoms in the individual alkyl moieties and, if present, 1 to 17 identical or different halogen atoms, or aryl, aryloxy, arylthio, arylamino, diarylamino, arylcarbonyl or arylsulphonyl, each of which has 6 to 10 carbon atoms in the individual aryl moieties and each of which is optionally monosubstituted or polysubstituted in the aryl moiety by identical or different substituents, or heterocyclyl which is optionally monosubstituted or polysubstituted by identical or different substituents, the aryl or heterocyclyl substituents in each case being selected from the group consisting of halogen, cyano, nitro, in each case straight-chain or branched alkyl, alkoxy or alkylthio each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents selected from the group consisting of halogen and straight-chain or branched alkyl having 1 to 4 carbon atoms;

or $R^3$ represents straight-chain or branched alkenyl which has 2 to 8 carbon atoms and which is optionally monosubstituted or polysubstituted by identical or different substituents selected from the group consisting of fluorine, chlorine, bromine, iodine, cyano, and aryl which has 6 to 10 carbon atoms and which is optionally monosubstituted or polysubstituted by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms;

or $R^3$ represents straight-chain or branched alkinyl which has 2 to 8 carbon atoms and which is optionally monosubstituted or polysubstituted by identical or different substituents selected from the group consisting of fluorine, chlorine, bromine and iodine;

or $R^3$ represents cycloalkyl or cycloalkenyl, each of which has 3 to 8 carbon atoms and each of which is optionally monosubstituted or polysubstituted by identical or different substituents selected from the group consisting of fluorine, chlorine, bromine, iodine, and in each case straight-chain or branched alkyl or halogenoalkyl, each of which has 1 to 8 carbon atoms, and if present, 1 to 17 identical or different halogen atoms;

or $R^3$ represents aryl which has 6 to 10 carbon atoms or heterocyclyl, and each aryl or heterocyclyl is optionally monosubstituted or polysubstituted by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted or polysubstituted by identical or different substituents selected from the group consisting of halogen and/or straight-chain or branched alkyl having 1 to 4 carbon atoms;

$R^4$ and $R^5$ independently of each other in each case represent hydrogen, straight-chain or branched alkyl having 1 to 8 carbon atoms, straight-chain or branched halogenoalkyl having 1 to 8 carbon atoms and 1 to 17 identical or different halogen atoms, or cycloalkyl having 3 to 8 carbon atoms, X represent oxygen or sulphur and Heterocyclyl represents a member selected from group consisting of pyridyl, furyl, tetrahydrofuranyl, thienyl, thiazolyl and triazolyl.

2. A substituted imidazolinylpyrimidine according to claim 1, in which $R^1$ represents hydrogen, fluorine, chlorine, bromine, iodine, cyano, nitro or thiocyanato;

or $R^1$ represents hydroxyl, mercapto, straight-chain or branched alkyloxy or alkylmercapto having 1 to 4 carbon atoms, straight-chain or branched halogenoalkyloxy or halogenoalkylmercapto having 1 to 4 carbon atoms and 1 to 9 identical or different halogen atoms, straight-chain or branched alkoxyalkyloxy or alkoxyalkylmercapto having in each case 1 to 4 carbon atoms in the individual alkyl moieties, straight-chain or branched dialkylaminoalkyloxy or dialkylaminoalkylmercapto having in each case 1 to 4 carbon atoms in the individual alkyl moieties, straight-chain or branched alkanoyloxy or alkanoylmercapto having 1 to 5 carbon atoms, straight-chain or branched alkoxycarbonyloxy or alkoxycarbonylmercapto having 2 to 5 carbon atoms, straight-chain or branched alkylsulphonyloxy or alkylsulphonylmercapto having 1 to 4 carbon atoms, straight-chain or branched alkoxysulphonyloxy or alkoxysulphonylthio having 1 to 4 carbon atoms, or arylalkyloxy or arylalkylthio which has 1 to 4 carbon atoms in the straight-chain or branched alkyl moiety and 6 or 10 carbon atoms in the aryl moiety, aryloxy or arylthio which has 6 or 10 carbon atoms, arylcarbonyloxy, arylcarbonylthio, arylsulphonyloxy, arylsulphonylthio, aryloxysulphonyloxy, aryloxysulphonylthio, heterocyclyloxy, heterocyclylthio, heterocyclylalkyloxy or heterocyclylalkylthio, each of which has, if present, 1 to 4 carbon atoms in the straight-chain or branched alkyl moiety, and each of these arylalkyl, aryl, arylcarbonyl, arylsulphonyl, aryloxysulphonyl, heterocyclyl or heterocyclylalkyl is optionally monosubstituted to pentasubstituted in the aryl or heterocyclyl moiety by identical or different substituents selected from the group consisting of halogen, cyano, nitro, in each case straight-chain or branched alkyl, alkoxy or alkylthio, each of which has 1 to 4 carbon atoms, in each straight-chain or branched halogenoalkyl, halogenoalkoxy or halogenoalkylthio, each of which has 1 to 4 carbon atoms, and 1 to 9 identical or different halogen atoms, and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted to pentasubstituted by identical or different substituents selected from the group consisting of halogen and straight-chain or branched alkyl having 1 to 4 carbon atoms;

or $R^1$ represents amino which is optionally monosubstituted or disubstituted by identical or different substituents selected from the group consisting of straight-chain or branched alkyl having 1 to 4 carbon atoms, straight-chain or branched alkenyl having 2 to 5 carbon atoms, straight-chain or branched alkinyl having 2 to 5 carbon atoms, straight-chain or branched halogenoalkyl having 1 to 4 carbon atoms and 1 to 9 identical or different halogen atoms, straight-chain or branched alkoxyalkyl having in each case 1 to 4 carbon atoms in the individual alkyl moieties, straight-chain or branched dialkylaminoalkyl, having in each case 1 to 4 carbon atoms in the individual alkyl moieties, straight-chain or branched alkanoyl having 1 to 4 carbon atoms, straight-chain or branched alkoxycarbonyl having 2 to 5 carbon atoms, straight-chain or branched alkylsulphonyl having 1 to 4 carbon atoms, straight-chain or branched alkoxysulphonyl having 1 to 4 carbon atoms, straight-chain or branched dialkylaminosulphonyl having in each case 1 to 4 carbon atoms in the individual alkyl moieties, or arylalkyl which has 1 to 4 carbon atoms in the straight-chain or branched alkyl moiety and 6 or 10 carbon atoms in the aryl moiety, aryl having 6 or 10 carbon atoms, arylcarbonyl, arylsulphonyl or aryloxysulphonyl, each of which has 6 or 10 carbon atoms in the aryl moiety, heterocyclyl or heterocyclylalkyl, each of which has, if present, 1 to 4 carbon atoms in the straight-chain or branched alkyl moiety, and each of these arylalkyl, aryl, arylcarbonyl, arylsulphonyl, aryloxysulphonyl, heterocyclyl and heterocyclylalkyl is optionally monosubstituted to pentasubstituted in the aryl or heterocyclyl moiety by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenaolkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and, if present, phenyl which is optionally monosubstituted to pentasubstituted by identical or different substituents selected from the group consisting of halogen and a straight-chain or branched alkyl having 1 to 4 carbon atoms;

or $R^1$ represents a carbonyl, sulphinyl or sulphonyl group, each of which is substituted by a member selected from the group consisting of hydrogen, hydroxyl, amino, in each case straight-chain or branched alkyl, alkoxy, alkylamino or dialkylamino, each of which has 1 to 4 carbon atoms in the individual alkyl moieties, in each case straight-chain or branched halogenoalkyl or halogenoalkoxy, each of which has 1 to 4 carbon atoms and 1 to 9 identical or different halogen atoms, or aryl, aryloxy, arylamino or diarylmino, each of which has 6 or 10 carbon atoms in the individual aryl moieties and each of which is optionally monosubstituted or pentasubstituted in the aryl moiety by a member selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted to pentasubstituted by identical or different substituents selected from the group consisting of halogen and straight-chain or branched alkyl having 1 to 4 carbon atoms;

or $R^1$ represents straight-chain or branched alkyl which has 1 to 6 carbon atoms and which is optionally monosubstituted to pentasubstituted by identical or different substituents selected from the group consisting of fluorine, chlorine, bromine, iodine, hydroxyl, cyano, nitro, aminocarbonyl, formamido, in each case straight-chain or branched alkoxy, halogenoalkoxy, alkylthio, halogenalkylthio, alkylamino, dialkylamino, alkanoyl, N-alkylaminocarbonyl, N,N-dialkylaminocarbonyl, alkanoylamido or alkylsulphonyl, each of which has 1 to 4 carbon atoms in the individual alkyl moieties and, if present, 1 to 9 identical or different halogen atoms, or aryl, aryloxy, arylthio, arylamino, diarylamino, arylcarbonyl or arylsulphonyl, each of which has 6 or 10 carbon atoms in the individual aryl moieties or heterocyclyl, and each of these aryl, aryloxy, arylthio, arylamino, diarylamino, arylcarbonyl, arylsulphonyl or heterocyclyl is optionally monosubstituted to pentasubstituted in the aryl or heterocyclyl moiety by a member selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual monosubstituted to pentasubstituted by identical or different substituents selected from the group consisting of halogen and/or straight-chain or branched alkyl having 1 to 4 carbon atoms;

or $R^1$ represents straight-chain or branched alkenyl which has 2 to 5 carbon atoms and which is optionally monosubstituted to trisubstituted by identical or different substituents selected from the group consisting of fluorine, chlorine, bromine, iodine and cyano;

or $R^1$ represents straight-chain or branched alkinyl which has 2 to 5 carbon atoms and which is optionally monosubstituted to trisubstituted by identical or different substituents selected from the group consisting of fluorine, chlorine, bromine and iodine;

or $R^1$ represents cycloalkyl or cycloalkenyl, each of which has 3 to 6 carbon atoms and each of which is optionally monosubstituted to pentasubstituted by identical or different substituents selected from the group consisting of fluorine, chlorine, bromine, iodine, and in each case straight-chain or branched alkyl or halogenoalkyl, each of which has 1 to 4 carbon atoms, and if present, 1 to 9 identical or different halogen atoms;

or $R^1$ represents aryl which has 6 or 10 carbon atoms or heterocyclyl, and each of these aryl or heterocyclyl is optionally monosubstituted to pentasubstituted by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted to pentasubstituted by identical or different substituents selected from the group consisting of halogen and straight-chain or branched alkyl having 1 to 4 carbon atoms;

$R^2$ represents hydrogen, hydroxyl, fluorine, chlorine, bromine, iodine, straight-chain or branched alkyl having 1 to 4 carbon atoms or straight-chain or branched halogenoalkyl having 1 to 4 carbon atoms and 1 to 9 identical or different halogen atoms, $R^3$ represents hydrogen or an equivalent of an alkali metal cation, alkaline earth metal cation or an ammonium cation which is optionally monosubstituted to tetrasubstituted by identical or different substituents selected from the group consisting of straight-chain or branched alkyl having 1 to 18 carbon atoms and/or benzyl, or $R^3$ represents straight-chain or branched alkyl which has 1 to 12 carbon atoms and which is optionally monosubstituted to pentasubstituted by identical or different substituents selected from the group consisting of fluorine, chlorine, bromine, iodine, hydroxyl, cyano, nitro, aminocarbonyl, formamido, in each case straight-chain or branched alkoxy, halogenoalkoxy, alkylthio, halogenoalkylthio, alkylamino, dialkylamino, alkanoyl, N-alkylaminocarbonyl, N,N-dialkylaminocarbonyl, alkanoylamido or alkylsulphonyl, each of which has 1 to 8 carbon atoms in the individual alkyl moieties and, if present, 1 to 17 identical or different halogen atoms, or aryl, aryloxy, arylthio, arylamino, diarylamino, arylcarbonyl or arylsulphonyl, each of which has 6 or 10 carbon atoms in the individual aryl moieties and each of which is optionally monosubstituted to pentasubstituted in the aryl moiety by identical or different substituents, or heterocyclyl which is optionally monosubstituted to pentasubstituted by identical or different substituents, the aryl or heterocyclyl substituents in each case being selected from the group consisting of halogen, cyano, nitro, each of case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted to pentasubstituted by identical or different substituents selected from the group consisting of halogen and straight-chain or branched alkyl having 1 to 4 carbon atoms;

or $R^3$ represents straight-chain or branched alkenyl which has 2 to 5 carbon atoms and which is optionally monosubstituted to trisubstituted by identical or different substituents selected from the group consisting of fluorine, chlorine, bromine, iodine or cyano, or aryl which has 6 or 10 carbon atoms and which is optionally monosubstituted to trisubstituted by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy, halogenoalkylthio, each of which has 1 to 4 carbon atoms and 1 to 9 identical or different halogen atoms;

or $R^3$ represents straight-chain or branched alkinyl which has 2 to 5 carbon atoms and which is optionally monosubstituted to trisubstituted by identical or different substituents selected from the group consisting of fluorine, chlorine, bromine and iodine;

or $R^3$ represents cycloalkyl or cycloalkenyl, each of which has 3 to 6 carbon atoms and each of which is optionally monosubstituted to pentasubstituted by identical or different substituents selected from the group consisting of fluorine, chlorine, bromine, iodine, and in each case straight-chain or branched alkyl or halogenoalkyl, each of which has 1 to 4 carbon atoms and, if present, 1 to 9 identical or different halogen atoms;

or $R^3$ represents aryl which has 6 or 10 carbon atoms or heterocyclyl, and each aryl or heterocyclyl is optionally monosubstituted to pentasubstituted by identical or different substituents selected from the group consisting of halogen, cyano, nitro, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms, in each case straight-chain or branched alkoxycarbonyl or alkoximinoalkyl, each of which has 1 to 4 carbon atoms in the individual alkyl moieties, and phenyl which is optionally monosubstituted to pentasubstituted by identical or different substituents selected from the group consisting of halogen and straight-chain or branched alkyl having 1 to 4 carbon atoms;

$R^4$ and $R^5$ independently of each other in each case represent hydrogen, straight-chain or branched alkyl having 1 to 4 carbon atoms, straight-chain or branched halogenoalkyl having 1 to 4 carbon atoms and 1 to 9 identical or different halogen atoms, or cycloalkyl having 3 to 6 carbon atoms and X represent oxygen or sulphur.

3. A substituted imidazolinylpyrimidine according to claim 1, in which $R^1$ represents hydrogen;

or $R^1$ represents hydroxyl, mercapto, straight-chain or branched alkyloxy or alkylthio, having 1 to 4 carbon atoms, straight-chain or branched alkoxyalkyloxy or alkoxyalkylthio having in each case 1 to 4 carbon atoms in the individual alkyl moieties, straight-chain or branched dialkylaminoalkyloxy or dialkylaminoalkylthio, having in each case 1 to 4 carbon atoms in the individual alkyl moieties, straight-chain or branched halogenoalkyloxy or halogenoalkylthio having 1 to 4 carbon atoms and 1 to 9 identical or different halogen atoms, or phenylalkyloxy or phenylalkylthio having 1 to 4 carbon atoms in the straight-chain or branched alkyl moiety or phenyloxy, phenylthio, pyridyloxy, pyridylthio, pyridylmethyloxy, pyridylmethylthio, furanylmethyloxy, furanylmethylthio, thienylmethyloxy, thienylmethylthio, thiazolylmethyloxy, thiazolylmethylthio, triazolylmethyloxy or triazolylmethylthio, and each of these phenylalkyl, phenyl, pyridyl, pyridylmethyl, furanylmethyl, thienylmethyl, thiazolylmethyl or triazolylmethyl moieties is optionally monosubstituted to trisubstituted in the phenyl or heteroaryl moiety by identical or different substituents, selected from the group consisting of halogen, in each case straight-chain or branched alkyl, alkoxy or alkylthio, each of which has 1 to 4 carbon atoms, in each case straight-chain or branched halogenoalkyl, halogenoalkoxy or halogenalkylthio, each of which has 1 to 4 carbon atoms and 1 to 9 identical or different halogen atoms;

or $R^1$ represents amino which is optionally monosubstituted or disubstituted by identical or different substituents selected from the group consisting of straight-chain or branched alkyl having 1 to 4 carbon atoms, allyl, propargyl, straight-chain or branched alkoxyalkyl having in each case 1 to 4 carbon atoms in the individual alkyl moieties, straight-chain or branched dialkylaminoalkyl having in each case 1 to 4 carbon atoms in the individual alkyl moieties, straight-chain or branched alkanoyl having 1 to 5 carbon atoms, straight-chain or branched alkoxycarbonyl having 2 to 5 carbon atoms, in each case straight-chain or branched alkylsulphinyl or alkylsulphonyl, each of which has 1 to 4 carbon atoms;

or $R^1$ represents a carbonyl, sulphinyl or sulphonyl group, each of which is substituted by a member selected from the group consisting of in each case straight-chain or branched alkyl, alkoxy, alkylamino and dialkylamino, each of which has 1 to 4 carbon atoms in the individual alkyl moieties;

or $R^1$ represents straight-chain or branched alkyl which has 1 to 6 carbon atoms and which is optionally monosubstituted to trisubstituted by identical or different substituents selected from the group consisting of:

fluorine, chlorine, in each case straight-chain or branched alkoxy or alkylthio, each of which has 1 to 4 carbon atoms, in each case straight-chain or branched halogenoalkoxy or halogenoalkylthio, each of which has 1 to 4 carbon atoms and 1 to 9 identical or different halogen atoms, or phenyl which is optionally monosubstituted or trisubstituted by identical or different substituents selected from the group consisting of halogen, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms;

or $R^1$ represents straight-chain or branched alkenyl having 3 to 6 carbon atoms;

or $R^1$ represents cyclopropyl which is optionally monosubstituted to trisubstituted by identical or different substituents selected from the group consisting or methyl and chlorine;

or $R^1$ represents phenyl which is optionally monosubstituted to trisubstituted by identical or different substituents selected from the group consisting of halogen, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms;

or $R^1$ represents pyridyl, furanyl, tetrahydrofuranyl, thienyl or thiazolyl, each of which is optionally monosubstituted to trisubstituted by identical or different substituents selected from the group consisting of in each case straight-chain or branched alkyl and alkoxy, each of which has 1 to 4 carbon atoms;

$R^2$ represents hydrogen or methyl, $R^3$ represents hydrogen or an equivalent of an alkali metal cation, alkaline earth metal cation or an ammonium cation which is optionally monosubstituted to tetrasubstituted by identical or different substituents selected from the group consisting of straight-chain or branched alkyl having 1 to 18 carbon atoms and/or benzyl;

or $R^3$ represents straight-chain or branched alkyl which has 1 to 12 carbon atoms and which is optionally monosubstituted to trisubstituted by identical or different substituents selected from the group consisting of fluorine, chlorine, hydroxyl, cyano, in each case straight-chain or branched alkoxy, alkylthio, alkylamino, dialkylamino, alkanoyl, N-alkylaminocarbonyl, N,N-dialkylaminocarbonyl, alkanoylamido or alkylsulphonyl, each of which has 1 to 8 carbon atoms in the individual alkyl moieties, in each case straight-chain or branched halogenoalkoxy or halogenoalkylthio, each of which has 1 to 8 carbon atoms and 1 to 17 halogen atoms, and phenyl, phenoxy, phenylthio, phenylamino, phenylcarbonyl, phenylsulphonyl, pyridyl, furanyl, tetrahydrofuranyl, thienyl or thiazolyl, each of which is optionally monosubstituted to trisubstituted in the phenyl or heteroaryl moiety by identical or different substituents selected from the group consisting of halogen, cyano, nitro, in each case straight-chain or branched alkyl, alkoxy, or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms;

or $R^3$ represents straight-chain or branched alkenyl having 2 to 6 carbon atoms;

or $R^3$ represents straight-chain or branched alkinyl having 2 to 6 carbon atoms;

or $R^3$ represents cyclopentyl or cyclohexyl, each of which is optionally monosubstituted to trisubstituted by identical or different substituents selected from the group consisting of fluorine, chlorine, and methyl;

or $R^3$ represents phenyl which is optionally monosubstituted to trisubstituted by identical or different substituents selected from the group consisting of halogen, in each case straight-chain or branched alkyl, alkoxy or alkylthio, each of which has 1 to 4 carbon atoms, in each case straight-chain or branched halogenoalkyl, halogenoalkoxy or halogenoalkylthio, each of which has 1 to 4 carbon atoms and 1 to 9 identical or different halogen atoms;

or $R^3$ represents pyridyl, furanyl, tetrahydrofuranyl, thienyl or thiazolyl, each of which is optionally substituted to trisubstituted by identical or different substituents, selected from the group consisting of in each case straight-chain or branched alkyl and alkoxy, each of which has 1 to 4 carbon atoms;

$R^4$ represents hydrogen, methyl or fluoromethyl, $R^5$ represents methyl, ethyl, n- or i-propyl or cyclopropyl and X represents oxygen or sulphur.

4. A substituted imidazolinylpyrimidine according to claim 1, in which $R^1$ represents hydrogen, hydroxyl, methoxy, ethoxy, n- or i-propoxy, n-, i-, s- or t-butoxy, trifluoromethoxy, mercapto, methylthio, ethylthio, n- or i-propylthio, n-, i-, s- or t-butylthio, trifluoromethylthio, benzylthio, 2-pyridylthio, amino, N-methylamino, N-ethylamino, N-n-propylamino, N-i-propylamino, N,N-dimethylamino, N,N-diethylamino, N-methyl-N-ethylamino, methylcarbonylamino, ethylcarbonylamino, methoxycarbonylamino, ethoxycarbonylamino, methylsulphinyl, ethylsulphinyl, methylsulphonyl, ethylsulphonyl, methyl, ethyl, n- or i-propyl, n-, i-, s- or t-butyl, n- or i-pentyl, n- or i-hexyl, fluoromethyl, trifluoromethyl, methoxymethyl, ethoxymethyl, methylthiomethyl, ethylthiomethyl, allyl, ethinyl, propargyl, cyclopropyl or represents phenyl which is optionally monosubstituted or disubstituted by identical or different substituents selected from the group consisting of fluorine, chlorine, bromine, methyl, ethyl, n- or i-propyl, n-, i-, s- or t-butyl, methoxy, ethoxy, n- or i-propoxy, n-, i-,1 s- or t-butoxy, methylthio, ethylthio, trifluoromethyl, trifluoromethoxy and trifluoromethylthio;

or $R^1$ represents pyridyl, furanyl, thienyl or thiazolyl, each of which is optionally monosubstituted or disubstituted by identical or different substituents selected from the group consisting of methyl, ethyl, n- or i-propyl, n-, i-, s- or t-butyl, methoxy, ethoxy, n- or i-propoxy, and n-, i-, s- or t-butoxy, $R^2$ represents hydrogen, $R^3$ represents hydrogen, a sodium ion, potassium ion, calcium ion or an ammonium ion which is optionally monosubstituted to tetrasubstituted by identical or different substituents selected from the group consisting of methyl, ethyl, n- or i-propyl, n-, i-, s- or t-butyl, n- or i-pentyl, n- or i-hexyl, n- or i-dodecyl and benzyl;

or $R^3$ represents methyl, ethyl, n-or i-propyl, n-, i-, s- or t-butyl, n- or i-pentyl, n-or i-hexyl, fluoromethyl, trifluoromethyl, hydroxyethyl, cyanoethyl, methoxyethyl, methylthioethyl, methylaminoethyl, ethylaminoethyl, N,N-dimethylaminoethyl, N,N-diethylaminoethyl, methylcarbonyl-methyl, methylcarbonylethyl, N-methylaminocarbonyl-methyl, N-methylaminocarbonylethyl, N-ethylaminocarbonylmethyl, N-ethylaminocarbonylethyl, N,N-dimethylaminocarbonylmethyl, N,N-diethylaminocarbonylmethyl, N,N-dimethylaminocarbonylethyl, N,N-diethyaminocarbonylethyl, N-acetylaminomethyl, N-acetylaminoethyl, N-propionylaminomethyl, N-propionylaminoethyl, methylsulphonylmethyl, methylsulphonylethyl, ethylsulphonylmethyl, ethylsulphonylethyl, allyl, propargyl, cyclopentyl, cyclohexyl or represents phenyl, pyridyl, benzyl or furanylmethyl, each of which is optionally monosubstituted to trisubstituted by identical or different substituents selected from the group consisting of fluorine, chlorine, bromine, cyano, nitro, methyl, ethyl, n- or i-propyl, n-, i-, s- or t-butyl, methoxy, ethoxy, n- or i-propoxy, n-, i-, s- or t-butoxy, methylthio, ethylthio, trifluoromethyl, trifluoromethoxy and trifluoromethylthio, $R^4$ represents methyl, $R^5$ represents isopropyl and X represents oxygen.

5. A compound according to claim 1, wherein such compound is 2-methyl-4-(4-methyl-4-isopropyl-imidazolin-5-on-2-yl)-pyrimidine-5-carboxylic-acid of the formula

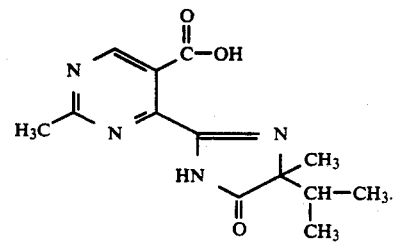

6. A compound according to claim 1, wherein such compound is 2-isopropyl-4-(4-methyl-4-isopropyl-imidazolin-5-on-2-yl)-pyrimidine-5-carboxylic-acid of the formula

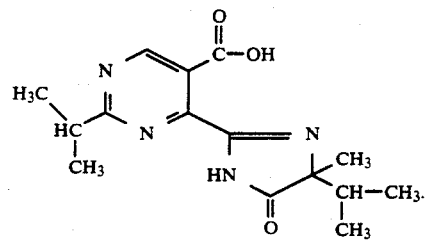

7. A compound according to claim 1, wherein such compound is 2-methylthio-4-(4-methyl-4-isopropyl-imidazolin-5-on-2-yl)-pyrimidine-5-carboxylic-acid of the formula

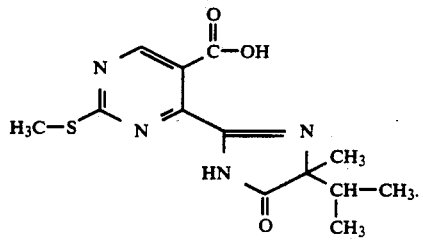

8. A compound according to claim 1, wherein such compound is 2-ethoxy-4-(4-methyl-4-isopropyl-imidazolin-5-on-2-yl)-pyrimidine-5-carboxylic-acid of the formula

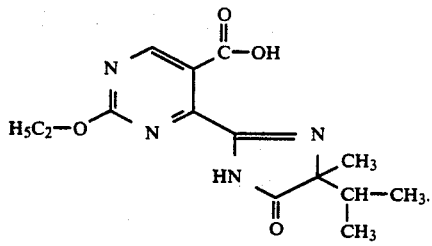

9. A herbicidal composition comprising a herbicidally effective amount of a compound according to claim 1, and a diluent.

10. A method of combating unwanted vegetation which comprises applying to such vegetation or to a locus from which it is desired to exclude such vegetation a herbicidally effective amount of a compound according to claim 1.

11. The method according to claim 10, wherein such compound is
2-methyl-4-(4-methyl-4-isopropyl-imidazolin-5-on-2-yl)-pyrimidine-5-carboxylic-acid,
2-isopropyl-4(4-methyl-4-isopropyl-imidazolin-5-on-2-yl)-pyrimidine-5-carboxylic-acid,
2-methylthio-4-(4-methyl-4-isopropyl-imidazolin-5-on-2-yl)-pyrimidine-5-carboxylic-acid,
2-ethoxy-4-(4-methyl-4-isopropyl-imidazolin-5-on-2-yl)-pyrimidine-5-carboxylic-acid.

* * * * *

UNITED STATES PATENT AND TRADEMARK OFFICE
CERTIFICATE OF CORRECTION

Page 1 of 2

PATENT NO. : 5,244,865
DATED : September 14, 1993
INVENTOR(S) : Seitz, et al.

It is certified that error appears in the above-identified patent and that said Letters Patent is hereby corrected as shown below:

Col. 37, line 25     Delete " hydroxy " and substitute -- hydroxyl --

Col. 38, line 32     After " 6 to 10 " insert -- carbon atoms --

Col. 42, line 39     After " each " insert -- case --

Col. 42, line 66     After " 1 to " delete " 4 " and substitute -- 5 --

Col. 43, line 23     Delete " halogenaolkoxy " and substitute -- halogenoalkoxy --

Col. 44, line 4     Delete " halogenalkylthio " and substitute -- halogenoalkylthio --

Col. 45, line 41     Delete " each of " and substitute -- in each --

Col. 47, line 10     Delete " halogenalkylthio " and substitute -- halogenoalkylthio --

UNITED STATES PATENT AND TRADEMARK OFFICE
CERTIFICATE OF CORRECTION

PATENT NO. : 5,244,865
DATED : September 14, 1993
INVENTOR(S) : Seitz, et al.

It is certified that error appears in the above-identified patent and that said Letters Patent is hereby corrected as shown below:

Col. 47, line 60    Delete " or " and substitute -- of --

Col. 49, line 30    After " n-,i-, " delete " 1 "

Signed and Sealed this

Third Day of August, 1999

Attest:

Attesting Officer

Q. TODD DICKINSON
Acting Commissioner of Patents and Trademarks